United States Patent
Oyadomari

(10) Patent No.: US 11,559,518 B2
(45) Date of Patent: Jan. 24, 2023

(54) ENDOPLASMIC RETICULUM STRESS REGULATOR COMPRISING BENZOTHIAZOIMIDAZOLYL COMPOUND

(71) Applicant: ER Stress Research Institute, Inc., Tokushima (JP)

(72) Inventor: Seiichi Oyadomari, Tokushima (JP)

(73) Assignee: ER STRESS RESEARCH INSTITUTE, INC., Tokushima (JP)

( * ) Notice: Subject to any disclaimer, the term of this patent is extended or adjusted under 35 U.S.C. 154(b) by 94 days.

(21) Appl. No.: 16/955,545

(22) PCT Filed: Dec. 25, 2018

(86) PCT No.: PCT/JP2018/047617
§ 371 (c)(1),
(2) Date: Jul. 7, 2020

(87) PCT Pub. No.: WO2019/131656
PCT Pub. Date: Jul. 4, 2019

(65) Prior Publication Data
US 2021/0386715 A1 Dec. 16, 2021

(30) Foreign Application Priority Data
Dec. 28, 2017 (JP) .............................. JP2017-255484

(51) Int. Cl.
| | |
|---|---|
| A61K 31/429 | (2006.01) |
| A61K 31/454 | (2006.01) |
| A61K 31/5377 | (2006.01) |
| A61P 39/06 | (2006.01) |
| C07D 513/04 | (2006.01) |

(52) U.S. Cl.
CPC .......... *A61K 31/429* (2013.01); *A61K 31/454* (2013.01); *A61K 31/5377* (2013.01); *A61P 39/06* (2018.01)

(58) Field of Classification Search
CPC ................ A61K 31/429; A61K 31/454; A61K 31/5377; A61P 39/06; C07D 513/04
See application file for complete search history.

(56) References Cited

U.S. PATENT DOCUMENTS 8,420,052 B2 * 4/2013 Kolb .................... C07D 513/14
424/1.89

FOREIGN PATENT DOCUMENTS

| EP | 2 696 859 | 2/2014 |
| EP | 2 968 347 | 11/2016 |

(Continued)

OTHER PUBLICATIONS

Balwe et al., Iron-catalyzed unprecedented formation of benzo[d]imidazo[2,1-b]thiazoles under solvent-free conditions, RSC Advances, vol. 6, No. 109, pp. 107225-107232 (Year: 2016).*

(Continued)

*Primary Examiner* — Brenda L Coleman
(74) *Attorney, Agent, or Firm* — Wenderoth, Lind & Ponack, L.L.P.

(57) ABSTRACT

A compound of general formula (1)

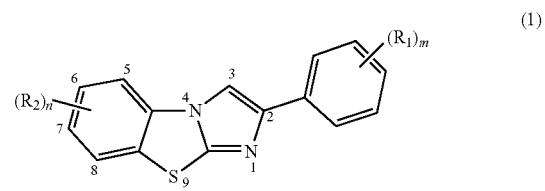

[wherein:

$R_1$ and $R_2$, which are the same or different, each represent a hydrogen atom, a halogen atom, a lower alkyl group, a lower cycloalkyl group, a lower alkanoyl group, a halogen substituted lower alkyl group, a lower alkoxy group, a halogen substituted lower alkoxy group, a cyano group, a cross-linked methylenedioxy group, an ethylenedioxy group, a propylenedioxy group, a lower alkylthio group, a lower alkylsulfonyl group, a carboxyl group, a lower alkoxycarbonyl group, a lower alkylamide group, a lower alkylamino alkylene amide group, an amino group, an alkylamino group, a hydroxy group, a functional group represented by general formula (2), or a functional group represented by general formula (3)

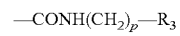

$$—CONH(CH_2)_p—R_3 \qquad (2)$$

[wherein $R_3$ represents a di-lower alkylamino group, a morpholino group, a piperidino group, a 2-methyl-piperidino group, or a 2-oxo-pyrrolidinyl group; p represents an integer from 2 to 6];

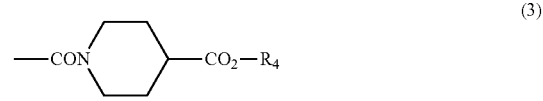

[wherein, $R_4$ represents a lower alkyl group];

m and n each represent an integer from 0 to 3;

the term lower represents a carbon number of 1 to 6; and the halogen atom represents a fluorine, chlorine or bromine atom] can inhibit endoplasmic reticulum stress to a greater extent as compared to known chemical chaperones. The compound thus can be used suitably as an agent for preventing, ameliorating or treating various diseases that are caused by endoplasmic reticulum stress.

11 Claims, 6 Drawing Sheets
Specification includes a Sequence Listing.

(56) References Cited

FOREIGN PATENT DOCUMENTS

| JP | 2001048786 | * | 2/2001 | ......... A61K 31/4188 |
|---|---|---|---|---|
| JP | 2014-512008 | | 5/2014 | |
| JP | 2016-517442 | | 6/2016 | |
| JP | 2017-193527 | | 10/2017 | |
| WO | 2012/108394 | | 8/2012 | |

OTHER PUBLICATIONS

Mishra et al., FeCl3/ZnI2-Catalyzed Synthesis of Benzo[d]imidazo[2,1-b]thiazole through Aerobic Oxidative Cyclization between 2-Aminobenzothiazole and Ketone, Organic Letters, vol. 16, No. 23, pp. 6084-6087 (Year: 2014).*

Ponnala et al., Synthesis of Bridgehead Nitrogen Heterocycles on a Solid Surface, Synthetic Communications, vol. 35, No. 11, pp. 2971-2975 (Year: 2005).*

Kim et al., "Cell death and endoplasmic reticulum stress: disease relevance and therapeutic opportunities", Nature Reviews Drug Discovery, vol. 7: 1013-1030 (2008).

Özcan et al., "Endoplasmic Reticulum Stress Links Obesity, Insulin Action, and Type 2 Diabetes", Science, vol. 306: 457-461 (2004).

Özcan et al., "Chemical Chaperones Reduce ER Stress and Restore Glucose Homeostasis in a Mouse Model of Type 2 Diabetes", Science, vol. 313: 1137-1140 (2006).

Reijonen et al., "Inhibition of endoplasmic reticulum stress counteracts neuronal cell death and protein aggregation caused by N-terminal mutant huntingtin proteins", Experimental Cell Research, 314: 950-960 (2008).

Baird et al., "Eukaryotic Initiation Factor 2 Phosphorylation and Translational Control in Metabolism", American Society for Nutrition. Adv. Nutr. 3: 307-321 (2012).

Costa-Mattioli et al., "Translational control of hippocampal synaptic plasticity and memory by the eIF2α kinase, GCN2", Nature, 436(7054): 1166-1173 (2005).

Sidrauski et al., "Pharmacological brake-release of mRNA translation enhances cognitive memory", eLife: 2:e00498 (2013), 22 pages.

Dey et al., "ATF4-dependent induction of heme oxygenase 1 prevents anoikis and promotes meastasis", Journal of Clinical Investigation, 125(7): 2592-2608 (2015).

Munn et al., "GCN2 Kinase in T Cells Mediates Proliferative Arrest and Anergy Induction in Response to Indoleamine 2,3-Dioxygenase", Immunity, 22: 633-642 (2005).

Miyake et al., "Skeletal muscle-specific eukaryotic translation initiation factor 2α phosphorylation controls amino acid metabolism and fibroblast growth factor 21-mediated non-cell-auto nomous energy metabolism", FASEB Journal, vol. 30: 798-812 (2016).

Kisoroukakenkyu, Biomedical Gerontology, 37 (3): 9-16 (2013) with Partial English translation.

Sayers et al., "Identification and Characterization of a Potent Activator of p53-Independent Cellular Senescence via a Small-Molecule Screen for Modifiers of the Integrated Stress Response", Mol. Pharmacol. vol. 83: 594-604 (2013).

Cortez et al., "The therapeutic potential of chemical chaperones in protein folding diseases", Prion, 8(2): 197-202 (2014).

Fu et al., "Phenotypic assays identify a small molecule modulator of the unfolded protein response with anti-diabetic activity", Sci Transl Med., 7(292): 1-28 (2015).

Tatzelt et al., "Chemical chaperones interfere with the formation of scrapie prion protein", The EMBO Journal, 15(23): 6363-6373 (1996).

International Search Report, dated Mar. 26, 2019 in corresponding International Patent Application No. PCT/JP2018/047617.

Oyadomari et al., "De-phosphorylation of translation initiation factor 2α (eIF2α) enhances glucose tolerance and attenuates hepatosteatosis in mice", Cell Metab., 7(6): 520-532 (2008).

* cited by examiner

SEQUENCE LISTING

```
<160> NUMBER OF SEQ ID NOS: 3

<210> SEQ ID NO 1
<211> LENGTH: 33
<212> TYPE: DNA
<213> ORGANISM: human

<400> SEQUENCE: 1
ggacgccgat tgggccacgt tgggagagtg cct                              33

<210> SEQ ID NO 2
<211> LENGTH: 27
<212> TYPE: DNA
<213> ORGANISM: human

<400> SEQUENCE: 2
ctcgagacag gtgctgacgt ggcattc                                      27

<210> SEQ ID NO 3
<211> LENGTH: 19
<212> TYPE: DNA
<213> ORGANISM: human

<400> SEQUENCE: 3
aacattgcat catccccgc                                               19
```

ENDOPLASMIC RETICULUM STRESS REGULATOR COMPRISING BENZOTHIAZOIMIDAZOLYL COMPOUND

SEQUENCE LISTING

A sequence listing in electronic (ASCII text file) format is filed with this application and incorporated herein by reference. The name of the ASCII text file is "2020_1654A_ST25.txt"; the file was created on Jul. 6, 2020; the size of the file is 1 KB.

TECHNICAL FIELD

The present invention relates to endoplasmic reticulum stress regulators. The endoplasmic reticulum stress regulator of the present invention has a function of controlling endoplasmic reticulum stress response (unfolded protein response: UPR). The endoplasmic reticulum stress regulator of the present invention is also a preventive or therapeutic agent for diseases caused by metabolic disorders, cranial nerve diseases, cancer, immune diseases and the like, based on its control function.

BACKGROUND ART

Living organisms are constantly exposed to a wide variety of external stress, and usually maintain homeostasis against such stress by control mechanisms such as the endocrine system. However, it is known that excessive stress sometimes causes not only mental health disorders but also physical stress reactions, which cause cerebrovascular disorders, heart diseases, digestive diseases, and even a decrease in immunity. On the other hand, cells are also exposed to internal and external stress at the cell level. Representative examples include viral infection, nutritional deficiency (deficiency of amino acids, sugars, lipids and the like), ischemia, heat shock and oxidative stress.

The endoplasmic reticulum is an important intracellular organelle involved protein synthesis. Nuclear-transcribed mRNAs are translated into proteins, which are taken up into the endoplasmic reticulum and folded correctly with the help of chaperones, and then secreted from the endoplasmic reticulum. However, when a molecule containing an inappropriate amino acid is involved, protein is incorrectly folded. Incorrectly folded proteins are processed by ERAD (ER-associated degradation), but when it exceeds processing capacity, abnormal proteins increase and endoplasmic reticulum (ER) stress is induced.

As shown in FIG. 1, it has turned out that incorrectly folded abnormal proteins increase in the endoplasmic reticulum due to environmental disturbance of the endoplasmic reticulum such as by viral infection, nutrient deficiency (amino acids, sugars, lipids), ischemia, heat shock and oxidative stress. This is called endoplasmic reticulum stress. It has been shown that the cells maintain their healthy condition by controlling endoplasmic reticulum function in response to environmental changes and adapting to the stress through endoplasmic reticulum stress response (UPR) when cells are exposed to endoplasmic reticulum stress. However, it has also become clear that when the endoplasmic reticulum stress response is disrupted, proteins are incorrectly folded and this results in the loss of function of the proteins necessary for the maintenance of life, and leads to a disease.

As shown in FIG. 2, by confirming the increase in the expression of endoplasmic reticulum stress markers, it is being clarified that endoplasmic reticulum stress or the disruption of endoplasmic reticulum stress response (UPR) is involved in the onset of various diseases (Non-patent Documents 5 to 12). For example, it is becoming understood that when cell dysfunction or cell death occurs due to severe endoplasmic reticulum stress, diseases such as diabetes, arteriosclerosis, neurodegenerative disease, autoimmune disease and cancer may develop. On the other hand, it has also been found that by enhancing the endoplasmic reticulum stress response (UPR), proliferative capacity is acquired even under a stressed condition, which leads to the development of cancer.

As shown in FIG. 3, there are mainly 3 pathways in the activation mechanism of endoplasmic reticulum stress response. In the 3 pathways, the accumulation of unfolded proteins in the endoplasmic reticulum is sensed by the activation of the endoplasmic reticulum stress transmission proteins (receptors), which are Ire1 (Inositol requiring enzyme 1), ATF6 (Activating transcription factor 6) and PERK (PKR-like endoplasmic reticulum kinase), respectively, and the information is transmitted to the cytosol and nucleus, and the endoplasmic reticulum stress response (UPR) is activated.

When the production of unfolded protein exceeds the protein folding capacity in the endoplasmic reticulum, a response to reduce this load on the endoplasmic reticulum takes place by first stopping protein synthesis (translational repression). This is controlled by the phosphorylation of eIF2α (eukaryotic initiation factor 2α subunit) necessary for translation initiation, by PERK.

PERK also targets transcription factor ATF4 and promotes the translation of ATF4. ATF4 binds to cis-factor AARE and induces the transcription of a series of genes to adapt cells to short-term stress.

Next, a molecular chaperone that carries out protein folding is induced in order to increase the protein folding capacity in the endoplasmic reticulum. This is mainly controlled by the activation of ATF6 by its cleavage into ATF6(N). XBP1 is a target gene of ATF6, and it is also a target of Ire1.

Furthermore, in order to remove the unfolded protein accumulated in the endoplasmic reticulum, the endoplasmic reticulum associated degradation (ERAD) is promoted in which the unfolded protein is exported from the endoplasmic reticulum to the cytosol for degradation by an ubiquitin proteasome system. This is mainly controlled by selective splicing of XBP1 (X-box-binding protein 1) by Ire1 into an active transcription factor.

When cells have disorders in which endoplasmic reticulum stress is unable to be removed even by means of such adaptive responses, they are eliminated by apoptosis, such as by inducing the expression of the proapoptotic transcription factor CHOP (C/EBP homologous protein).

Recently, drug discovery targeting endoplasmic reticulum stress response and integrated stress response has attracted attention (Patent Documents 1 to 3). For example, a low molecular weight compound. Salubrinal, has been identified by a search for a compound that avoids neuronal cell death caused by endoplasmic reticulum stress. Salubrinal reduces endoplasmic reticulum stress by suppressing the dephosphorylation of eIF2α (by accelerating the phosphorylation of eIF2α), and suppressing the synthesis of proteins that become unfolded proteins (Non-patent Document 4).

A chemical chaperone, which is a low molecular weight compound that complements or assists the function of the original molecular chaperone (protein chaperone) has been considered as therapeutic method giving thought to relieving endoplasmic reticulum stress. 4PBA and its improved form, TUDCA, have been reported so far to improve pathological conditions such as insulin resistance in type 2 diabetes model mice (Non-patent Document 3). 4PBA and TUDCA have no effect unless administered in large amounts, however, Azoramide, which has an antidiabetic effect at a lower concentration, has been recently reported.

Drug discovery research targeting the endoplasmic reticulum stress response and integrated stress response has developed accordingly, however, there are only little knowledge as to the core structure necessary to create compounds that can be used for the prevention or treatment of various diseases (metabolic disorders, cranial nerve diseases, cancer, immune diseases, etc.).

CITATION LIST

Patent Documents

[Patent Document 1] Japanese Unexamined Patent Re-Publication No. 2012-108394
[Patent Document 2] Japanese Unexamined Patent Publication No. 2014-512008
[Patent Document 3] Japanese Unexamined Patent Publication No. 2016-517442

Non-Patent Documents

[Non-Patent Document 1] Kim et al. Nat. Rev. Drug. Discov. 7 (12): 1013-30(2008)
[Non-Patent Document 2] Ozcan et al. Science 306, 457-461 (2004)
[Non-Patent Document 3] Ozcan et al. Science 313, 1137-1140 (2006)
[Non-Patent Document 4] Reijonen et al. Exp Cell Res 314, 950-960 (2008)
[Non-Patent Document 5] Oyadomari et al. Cell Metab 7, 520-532 (2008).
[Non-Patent Document 6] Baird et al, Adv Nutr 3, 307-321 (2012).
[Non-Patent Document 7] Costa-Mattioli et al. Nature 436, 1166-1173 (2005).
[Non-Patent Document 8] Sidrauski et al. Elife 2, e00498 (2013).
[Non-Patent Document 9] Dey et al. J Clin Invest, 125, 2592-2608 (2015).
[Non-Patent Document 10] Munn et al. Immunity, 22, 633-642 (2005).
[Non-Patent Document 11] Oyadomari et al, FAEB J. 30, 798-812 (2016)
[Non-Patent Document 12] KISOROUKAKENKYU (Biomedical Gerontology) 37 (3); 9-16, 2013

SUMMARY OF INVENTION

Technical Problem

The object of the present invention is to provide a novel compound that is capable of controlling endoplasmic reticulum stress in order to develop therapeutic agents for diseases that result from endoplasmic reticulum stress and integrated stress.

Solution to Problem

The inventor of the present invention generated a genetically modified mouse in which endoplasmic reticulum stress response signals are able to be controlled, in order to evaluate the effect of integrated stress, in particular endoplasmic reticulum that occurs organ-specifically (liver adipocyte, skeletal muscle), and has revealed about regulation of biological function due to endoplasmic reticulum stress response. Further, the present inventor has newly developed a cell evaluation system that is capable of quantifying the endoplasmic reticulum stress response signals with a higher sensitivity and more conveniently than conventional systems (FIG. 4). An attempt was made to identify a compound that is capable of reducing endoplasmic reticulum stress by means of a compound library screening using this cell evaluation system constructed by the present inventor. Compounds that have chemical chaperone activity will suppress or abolish the activation of endoplasmic reticulum stress response induced under endoplasmic reticulum stress, therefore, they can be discovered by utilizing the above-mentioned evaluation system. Compounds with chemical chaperone activity are expected to be useful in the prevention and treatment of various diseases by reducing endoplasmic reticulum stress. In particular, endoplasmic reticulum stress related to insulin and insulin receptors have attracted attention with respect to the onset of diabetes, and the onset of diabetes should be prevented if pancreatic β cells can be protected from endoplasmic reticulum stress related to insulin secretion.

The screening system constructed by the present inventor is a cell-based screening method, therefore, there may have been false-positive hit compounds due to the reduction of cell viability or acting on a reporter protein. Accordingly, the false-positive compounds were excluded by performing a cytotoxicity assay as well as EGFP reporter and luciferase reporter assays that detect the endoplasmic reticulum stress response with the administration of a high concentration (100 μM).

As a result of re-assaying the compounds discovered, the following benzothiazoimidazolyl compounds of general formula (1) were found to have stronger endoplasmic reticulum stress reducing effects than known chemical chaperones.

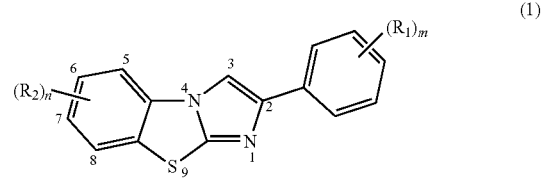

(1)

[wherein:
$R_1$ and $R_2$ which are the same or different, each represent a hydrogen atom, a halogen atom, a lower alkyl group, a lower cycloalkyl group, a lower alkanoyl group, a halogen substituted lower alkyl group, a lower alkoxy group, a halogen substituted lower alkoxy group, a cyano group, a cross-linked methylenedioxy group, an ethylenedioxy group, a propylenedioxy group, a lower alkylthio group, a lower alkylsulfonyl group, a carboxyl group, a lower alkoxycarbonyl group, a lower alkylamide group, a lower alkylamino alkylene amide group, an amino group, an alkylamino group, a hydroxy group, a functional group represented by general formula (2), or a functional group represented by general formula (3)

(2)

[wherein, $R_3$ represents a di-lower alkylamino group, a morpholino group, a piperidino group, a 2-methyl-piperidino group or a 2-oxo-pyrrolidinyl group; p represents an integer from 2 to 6];

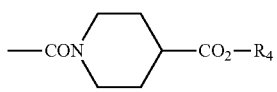

[wherein, $R_4$ represents a lower alkyl group]; and m and n each represent an integer from 0 to 3.]

The present inventor has completed the present invention based on the above discovery.

Specifically, the gist of the present invention is as follows.

[1] An endoplasmic reticulum stress regulator comprising as an active ingredient a benzothiazoimidazolyl compound represented by general formula (1)

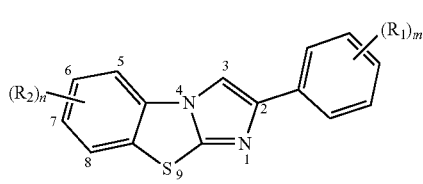

[wherein: $R_1$ and $R_2$, which are the same or different, each represent a hydrogen atom, a halogen atom, a lower alkyl group, a lower cycloalkyl group, a lower alkanoyl group, a halogen substituted lower alkyl group, a lower alkoxy group, a halogen substituted lower alkoxy group, a cyano group, a cross-linked methylenedioxy group, an ethylenedioxy group, a propylenedioxy group, a lower alkylthio group, a lower alkylsulfonyl group, a carboxyl group, a lower alkoxycarbonyl group, a lower alkylamide group, a lower alkylamino alkylene amide group, an amino group, an alkylamino group, a hydroxy group, a functional group represented by general formula (2), or a functional group represented by general formula (3)

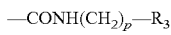

[wherein, $R_3$ represents a di-lower alkylamino group, a morpholino group, a piperidino group, a 2-methyl-piperidino group, or a 2-oxo-pyrrolidinyl group; p represents an integer from 2 to 6];

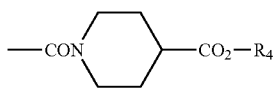

[wherein, $R_4$ represents a lower alkyl group]; m and n each represent an integer from 0 to 3; the term lower represents a carbon number of 1 to 6; and the halogen atom represents a fluorine, chlorine or bromine atom].

[2] The endoplasmic reticulum stress regulator according to [1], wherein $R_1$ is a hydrogen atom, a halogen atom, a lower alkyl group, a lower alkoxy group, a halogen substituted lower alkoxy group, a hydroxy group, or an amide group, and in is either 1 or 2.

[3] The endoplasmic reticulum stress regulator according to [1] or [2], wherein m is 1 and $R_1$ is substituted at para-position, or m is 2 and $R_1$ is substituted at para- and meta-positions.

[4] The endoplasmic reticulum stress regulator according to [2] or [3], wherein the halogen atom of $R_1$ is a fluorine or chlorine atom, the lower alkyl group of $R_1$ is a methyl or ethyl, and the lower alkoxy group of $R_1$ is a methoxy or ethoxy.

[5] The endoplasmic reticulum stress regulator according to any one of [1] to [4], wherein $R_2$ is a hydrogen atom, a lower alkyl group, a lower alkylsulfonyl group, a carboxyl group, a lower alkoxycarbonyl group, a substituent represented by the general formula (2), or a substituent represented by the general formula (3), and n is 1.

[6] The endoplasmic reticulum stress regulator according to [5], wherein the lower alkyl group of $R_2$ is a methyl, the lower alkylsulfonyl group of $R_2$ is a methylsulfonyl, and the lower alkoxycarbonyl group of $R_2$ is a methoxycarbonyl or ethoxycarbonyl.

[7] The endoplasmic reticulum stress regulator according to [5], wherein the di-lower alkylamino group of in the general formula (2) is a diethylamino, the 2-alkyl-piperidino group of $R_3$ is a 2-methyl-piperidino, and p is 3.

[3] The endoplasmic reticulum stress regulator according to [5], wherein the lower alkyl group of $R_4$ in the general formula (3) is a methyl or ethyl.

[9] The endoplasmic reticulum stress regulator according to any one of [1] to [8], wherein n is 1, and $R_2$ is a 7-position substituent.

[10] The endoplasmic reticulum stress regulator according to [1], wherein:

n and m are 1, and $R_1$ is a hydrogen atom, chlorine atom, fluorine atom, methyl, ethyl, methoxy, ethoxy, difluoromethoxy or trifluoromethozy substituted at para-position, a fluorine atom substituted at ortho-position, or a methoxy or ethoxy substituted at metha-position, and $R_2$ is a hydrogen atom, methoxycarbonyl, ethoxycarbonyl, methylsulfonyl, 3-(diethylamino)-propylamide, 3-piperidino-propylamide, 3-(2-methyl-piperidino)-propylamide, 3-morpholino-propylamide or 4-ethoxycarbonylpiperidinocarbonyl substituted at 7-position; or n is 1 and m is 2, and $R_1$ is a hydroxy group substituted at para-position and an amide group substituted at metha-position, and $R_2$ is a hydrogen atom.

[11] The endoplasmic reticulum stress regulator according to [1], wherein:

n and m are 1, and $R_1$ is a hydrogen atom, chlorine atom, methyl, ethyl, methoxy, difluoromethoxy or trifluoromethoxy substituted at pare-position, a fluorine atom substituted at ortho-position, or a methoxy or ethoxy substituted at metha-position, and $R_2$ is a hydrogen atom, methoxycarbonyl, ethoxycarbonyl, methylsulfonyl, 3-(diethylamino)-propylamide, 3-(2-methyl-piperidino)-propylamide or 3-morpholino-propylamide substituted at 7-position; or n is 1 and m is 2, and $R_1$ is a hydroxyl group substituted at para-position and an amide group substituted at metha-position, and $R_2$ is a hydrogen atom.

[12] An endoplasmic reticulum stress regulator comprising as an active ingredient the benzothiazoimidazolyl compound according to [1] represented by general formula (5)

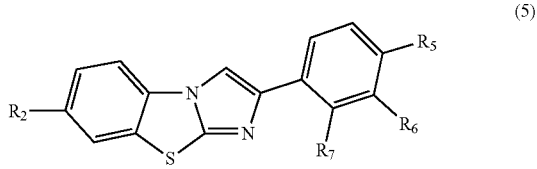

(5)

[wherein:
$R_5$, $R_6$, and $R_7$ each independently represent a hydrogen atom, fluorine atom, chlorine atom, methoxy, ethoxy, difluoromethoxy, trifluoromethoxy, methyl or ethyl, and $R_2$ represents a hydrogen atom, methyl, ethyl, isopropyl, carboxyl, ester group, amide group, methylsulfonyl, ethylsulfonyl or isopropylsulfonyl;
the ester group represents a methoxycarbonyl, ethoxycarbonyl or isopropyloxycarbonyl;
the amide group represents a 3-N-morpholino-propylaminocarbonyl, 3-N-piperidino-propylaminocarbonyl, 3-N-(2-methyl-piperidino)-propylaminocarbonyl, 3-N-(2-pyrrolidone)-propylaminocarbonyl, 3-(diethylamino)-propylaminocarbonyl or N-(4-ethoxycarbonylpiperidino)-carbonyl].

[13] The endoplasmic reticulum stress regulator according to [12], wherein $R_2$ is a hydrogen atom, methylsulfonyl, hydrogen atom, methoxycarbonyl, ethoxycarbonyl, 3-(diethylamino)-propylamide, 3-(2-methyl-piperidino)-propylamide or 3-morpholino-propylamide.

[14] The endoplasmic reticulum stress regulator according to [12] or [13], wherein $R_5$ is a hydrogen atom, fluorine atom, chlorine atom, methoxy, ethoxy, hydroxy, methyl, ethyl or difluoromethoxy.

[15] The endoplasmic reticulum stress regulator according to any one of [12] to [14], wherein $R_6$ is, a methoxy, ethoxy or aminocarbonyl group.

[16] The endoplasmic reticulum stress regulator according to any one of [12] to [15], wherein $R_7$ is a fluorine atom.

[17] The endoplasmic reticulum stress regulator according to any one of [1] to [16], wherein the endoplasmic reticulum stress regulator is an agent for accelerating eIF2α phosphorylation.

[18] The endoplasmic reticulum stress regulator according to any one of [1] to [17], wherein the 50% inhibitory concentration ($IC_{50}$) of the compound against cell death due to endoplasmic reticulum stress under the coexistence of Tunicamycin is 20 μM or less, preferably 10 μM or less, more preferably 5 μM or less, and more preferably 1 μM or less.

[19] An agent for preventing, ameliorating or treating a neurodegenerative disease or a lifestyle-related disease (metabolic syndrome), comprising the endoplasmic reticulum stress regulator according to any one of [1] to [18].

[20] An agent for prevention, amelioration or treatment according to [19], wherein the neurodegenerative disease is Alzheimer's disease or Parkinson's disease.

[21] An agent for prevention, amelioration or treatment according to [19], wherein the lifestyle-related disease is diabetes.

[22] An agent for preventing, ameliorating or treating a pancreatic β cell damage comprising the endoplasmic reticulum stress regulator according to any one of [1] to [18].

Advantageous Effects of Invention

The compound represented by general formula (1), decreased the activities of the endoplasmic reticulum stress markers ERSE2, UPPE, and AARE that were increased by endoplasmic reticulum stress loading, and made them recover to the same extent as when endoplasmic reticulum stress was not loaded. This action was stronger than the existing chemical chaperones Azoramide, 4PBA and TUDCA. With regard to the endoplasmic reticulum stress reducing effect of the compound represented by general formula (1), 50% inhibitory concentration ($IC_{50}$) of the compound against cell death due to endoplasmic reticulum stress under the coexistence of Tunicamycin was 20 μM or less.

The compound represented by general formula (1), reduced the levels of expression of endoplasmic reticulum stress markers GADD34, ATF4 and CHOP that were increased by endoplasmic reticulum stress loading and made them recover to the same extent as those in the case where endoplasmic reticulum stress was not loaded, and this action was stronger than Azoramide.

In addition, the compound represented by general formula (1) effectively restored cell proliferation that was inhibited by endoplasmic reticulum stress loading, and this action was stronger than Azoramide. In addition, the compound represented by general formula (1) restored intracellular ATP level (indicator of cell viability) that was decreased by endoplasmic reticulum stress loading to the same extent as that in the case where endoplasmic reticulum stress was not loaded. Additionally, the compound represented by general formula (1) decreased activity of lactate dehydrogenase (indicator of cell membrane damage) that was increased by endoplasmic reticulum stress loading to the same extent as that in the case where endoplasmic reticulum stress was not loaded. This action was stronger than Azoramide. Furthermore, the compound represented by general formula (1) restored cell proliferation that was suppressed due to the expression of abnormally folded prion proteins.

Thus, the compound represented by general formula (1) effectively protects cells from endoplasmic reticulum stress. In particular, it effectively protects cells that express abnormally folded prion proteins, which are found in neurodegenerative diseases.

As mentioned above, endoplasmic reticulum stress causes various diseases. For example, neurodegenerative diseases such as Parkinson's disease, polyglutamine disease, Alzheimer's disease and amyotrophic lateral sclerosis (ALS) are characterized by an excessive accumulation of structurally abnormal proteins in the neuronal cells as a result of endoplasmic reticulum stress.

In addition, PERK and Ire1, which are endoplasmic reticulum stress sensors, are abundantly present in the endoplasmic reticulum of pancreatic β cells. Generally, endoplasmic reticulum stress response maintains the endoplasmic reticulum homeostasis and insulin is normally secreted, however, when very strong endoplasmic reticulum stress is generated, β cells undergo apoptosis and insulin is not secreted normally, therefore developing diabetes.

Strong endoplasmic reticulum stress also causes various other diseases such as arteriosclerosis, cancer, and immune diseases (Non-patent Documents 5 to 12).

Accordingly, the compound represented by general formula (1) is effective in relieving endoplasmic reticulum stress of pancreatic β cells, and is effective, as an agent for preventing, ameliorating or treating pancreatic β cell damage. Furthermore, it can be used as a drug for preventing, ameliorating or treating lifestyle-related diseases such as diabetes (which are often triggered by metabolic syndrome). In addition, it can also be used as a drug for preventing, ameliorating or treating neurodegenerative diseases such as Parkinson's disease, cancer and immune diseases, in which endoplasmic reticulum stress is known to be involved.

DESCRIPTION OF EMBODIMENTS

Figure 1:
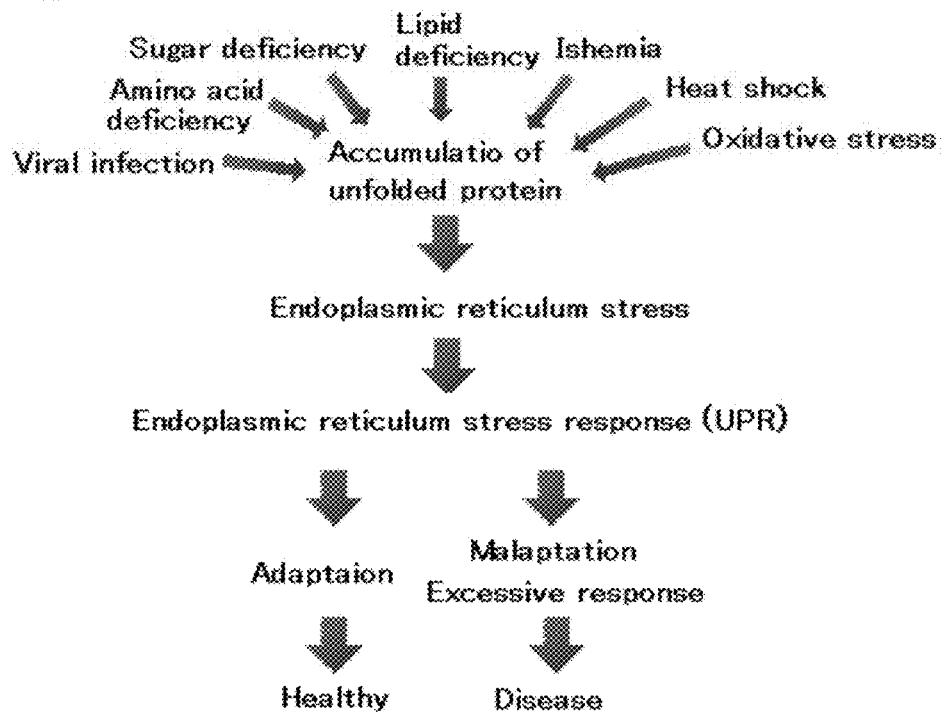
FIG. 1 depicts the causes and effects of endoplasmic reticulum stress and endoplasmic reticulum stress response (UPR).
Figure 2:
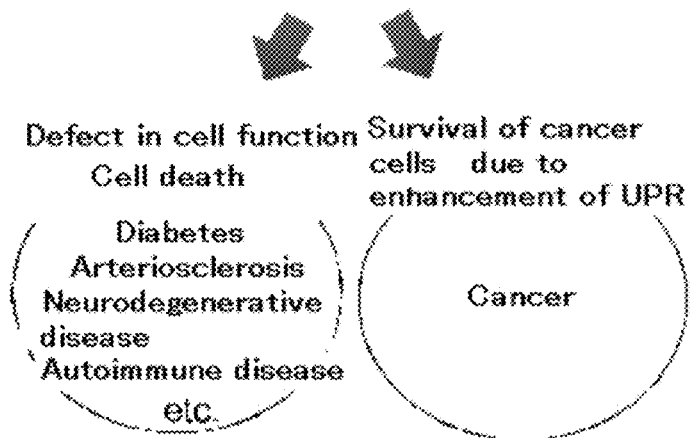
FIG. 2 depicts an overview of the diseases that are caused by endoplasmic reticulum stress.
Figure 3:
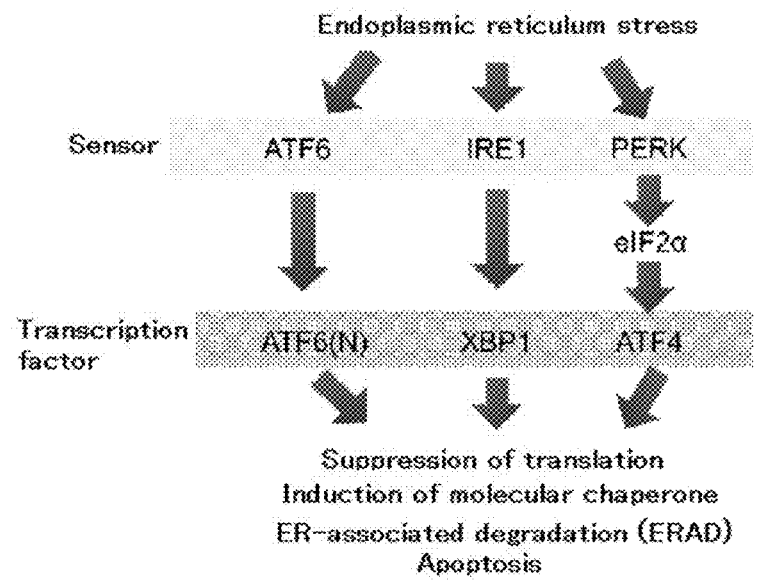
FIG. 3 depicts the mechanism in which intracellular proteins are expressed and activated in response to endoplasmic reticulum stress.

In the benzothiazoimidazolyl compound of the present invention represented by general formula (1), $R_1$ and $R_2$ are the same or different, and each represent a hydrogen atom, a halogen atom, a lower alkyl group, a lower cycloalkyl group, a lower alkanoyl group, a halogen substituted lower alkyl group, a lower alkoxy group, a halogen substituted lower alkoxy group, a cyano group, cross-linked methylenedioxy group, an ethylenedioxy group, a propylenedioxy group, a lower alkylthio group, a lower alkylsulfonyl group, a carboxyl group, a lower alkoxycarbonyl group, an aminocarboxyl group, a lower alkylamide group, a lower alkylamino alkylene amide group, an amino group, an alkylamino group, a hydroxy group, a functional group represented by general formula (2), or a functional group represented by general formula (3).

$$—CONH(CH_2)_p—R_3 \qquad (2)$$

$R_3$ represents a di-lower alkylamino group, a morpholino group, a piperidino group, or a 2-oxo-pyrrolidinyl group. These substituents can be substituted by lower alkyl group(s) such as methyl and ethyl, lower alkoxycarbonyl group(s), fluorine atom(s) and chlorine atom(s). Examples include 2-lower alkyl-piperidino groups such as 2-methyl-piperidino and 2-ethyl-piperidino, and 4-lower alkoxy carbonyl-piperidino groups such as 4-methoxycarbonyl-piperidino and 4-ethoxycarbonyl-piperidino.

Preferable examples of $R_3$ include di-lower alkylamino groups such as diethylamino and dimethylamino, morpholino, piperidino and 2-alkyl-piperidino groups such as 2-methyl-piperidino.

p represents an integer from 2 to 6. Preferably, the integer is 3 or 4, and more preferably 3.

Preferable examples of the functional group represented by general formula (2) include 3-(di-lower alkylamino)-propylamide groups such as 3-(dimethylamino)-propylamide and 3-(diethylamino)-propylamide, 3-piperidino-propylamide, 3-(2-lower alkyl-piperidino)-propylamide groups such as 3-(2-methyl-piperidino)-propylamide and 3-(2-ethyl-piperidino)-propylamide, and 3-morpholino-propylamide.

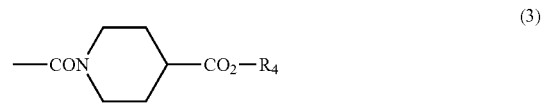

(3)

$R_4$ represents a lower alkyl group, preferably methyl or ethyl. Preferable examples of the functional group represented by the general formula (3) include 4-lower alkoxycarbonyl piperidino carbonyl groups such as 4-methoxycarbonyl piperidino carbonyl and 4-ethoxycarbonyl piperidino carbonyl.

In the present invention, the term lower refers to carbon number 1 to 6, preferably carbon number 1 to 4, and more preferably carbon number 1 to 3, unless otherwise specified. A halogen atom refers to a fluorine, chlorine or bromine atom.

m and n each represent an integer from 0 to 3. Preferably, m and n can independently represent an integer of 0 or 1. It is also preferred that n is 1 and m is 2.

$R_1$ is a phenyl ring substituent, and there are three sites of substitution, the ortho, meta, and para positions, when m is 2, a combination of para and meta positions is preferred.

Preferable $R_1$ includes a hydrogen atom, a halogen atom such as fluorine or chlorine atom, a lower alkyl group such as methyl or ethyl, a lower alkoxy group such as methoxy or ethoxy, or a halogen-substituted lower alkoxy croup such as difluoromethoxy or trifluoromethoxy.

$R_2$ is a substituent at the 6 to 8 positions of the benzothiazoimidazolyl skeleton, and preferably at the 7 position. Preferable $R_2$ includes a hydrogen atom, a carboxyl group, a lower alkyl group such as methyl, a lower alkylsulfonyl group such as methylsulfonyl, ethylsulfonyl, propylsulfonyl or isopropylsulfonyl, a lower alkoxycarbonyl group such as methoxycarbonyl, ethoxycarbonyl, propyloxycarbonyl or isopropyloxycarbonyl, substituent represented by general formula (2), or substituents represented by general formula (3).

The compounds listed in the following list of compounds exemplifies the compound of general formula (1) of the present invention. A compound having endoplasmic reticulum stress relieving activity at a lower concentration than known chemical chaperones that relieve endoplasmic reticulum stress Azoramide, 4PBA and TUDCA) are preferable among others.

List of Compounds

Compound No. 1

Compound No. 2

Compound No. 3

Compound No. 4

Compound No. 5

Compound No. 6

Compound No. 7

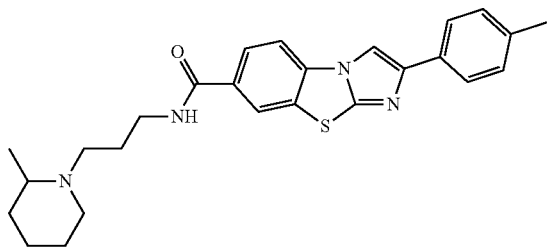

Compound No. 8

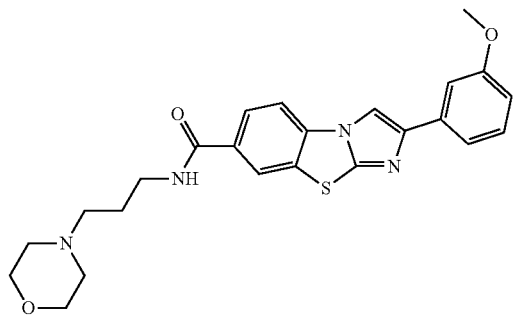

Compound No. 9

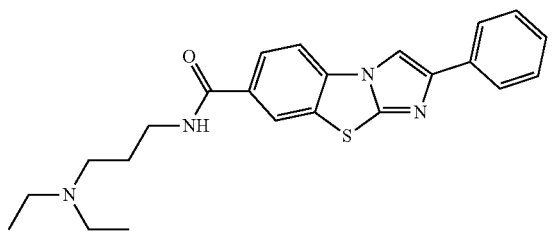

Compound No. 10

Compound No. 11

Compound No. 12

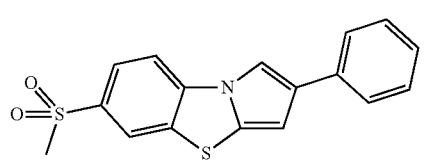
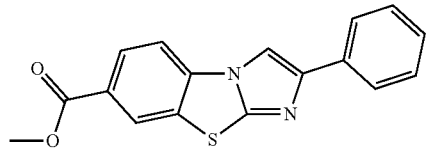
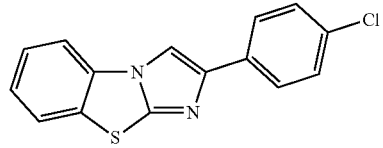
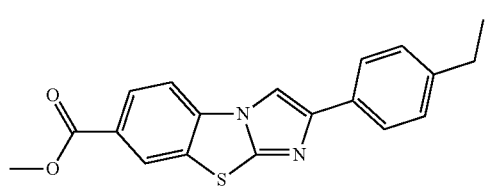
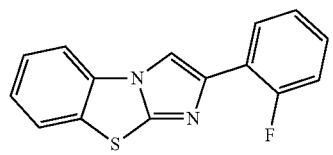
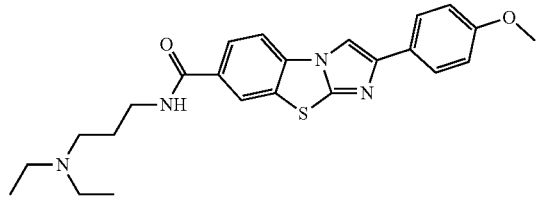
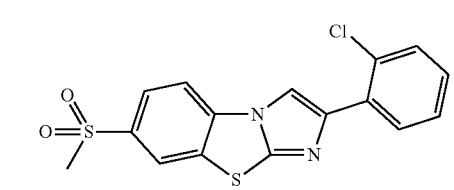

Compound No. 13
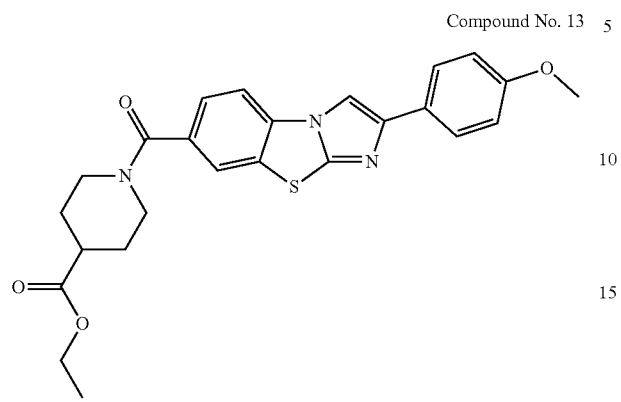
Compound No. 14
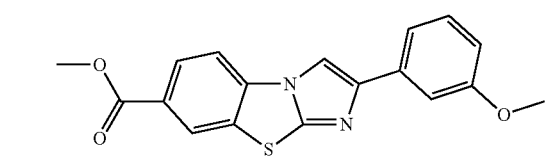
Compound No. 15
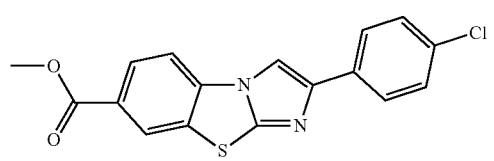
Compound No. 16
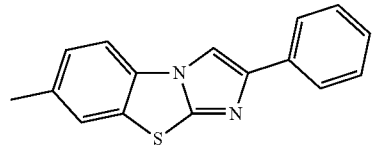
Compound No. 17
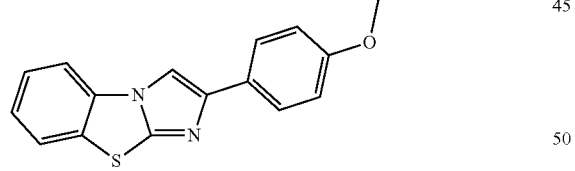
Although Compound No. 17 is a hydrobromide, the active ingredient of the endoplasmic reticulum stress regulator of the present invention also comprises the following compound.
Compound No. 18
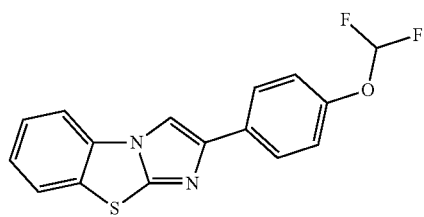
Compound No. 19
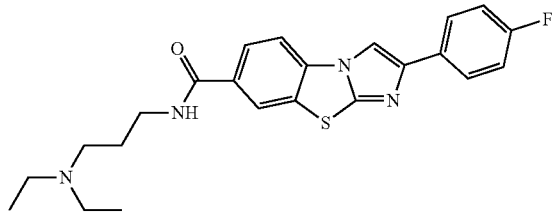
Compound No. 20
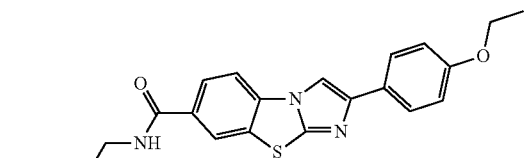
Compound No. 21
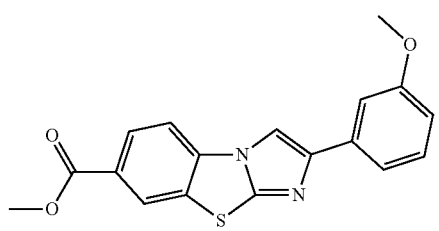
Compound No. 22
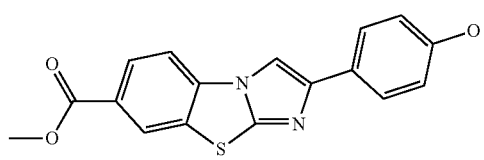
Compound No. 23
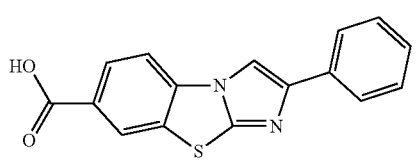
Compound No. 24
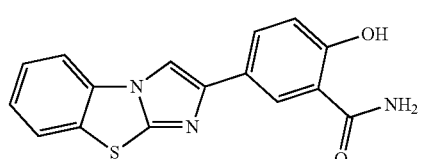

Compound No. 25

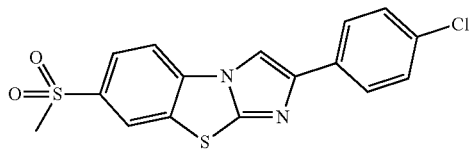

In addition, the following compound (4) is exemplified as compound of formula (1) of the present invention.

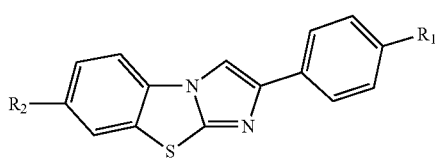

(4)

$R_1$ and $R_2$ in formula (4) represent functional groups indicated in Table 1.

TABLE 1

| Compound No. | $R_1$ | $R_2$ |
|---|---|---|
| 26 | $OCF_3$ | $SO_2CH_3$ |
| 27 | CL | $SO_2C_2H_5$ |
| 28 | CL | $SO_2CH(CH_3)_2$ |
| 29 | CL | $CO_2H$ |
| 30 | CL | $CH_3$ |
| 31 | CL | $CO_2C_2H_5$ |
| 32 | CL | $CO_2CH(CH_3)_2$ |
| 33 | $CH_3$ | H |
| 34 | $CH_3$ | $CO_2CH(CH_3)_2$ |

The compound represented by general formula (1) of the present invention can be manufactured according to methods known in the art. For example, the method for synthesis can include the following steps a) to c).

a) Synthesis Example of Benzothiazoimidazole Skeleton

An aniline derivative is reacted with ammonium isothiocyanate in the presence of bromine to synthesize aminobenzothiazole, and condensation ring closure reaction is performed with a chloroacetophenone derivative in the presence of a base (potassium carbonate), to obtain 2-phenyl benzothiazoimidazole (1).

b) Synthesis Example of Amide Derivative

An ester is hydrolyzed to synthesize a carboxylic acid derivative, and reaction is carried out using a corresponding amine derivative and a condensing agent such as DCC (dicyclohexylcarbodiimide) to obtain an amide derivative (1-1).

c) Synthesis Example of Methylsulfonyl Derivative

Anion is formed with butyllithium, and subsequently, reacted with dimethyldisulfide to introduce a methylthio group, and oxidation is performed with a peracid such as mCPBA (m-chloroperbenzoic acid) to obtain 2-phenyl-7-methylsulfonylbenzothiazoimidazole (1-2).

The steps a) to c) are illustrated below.

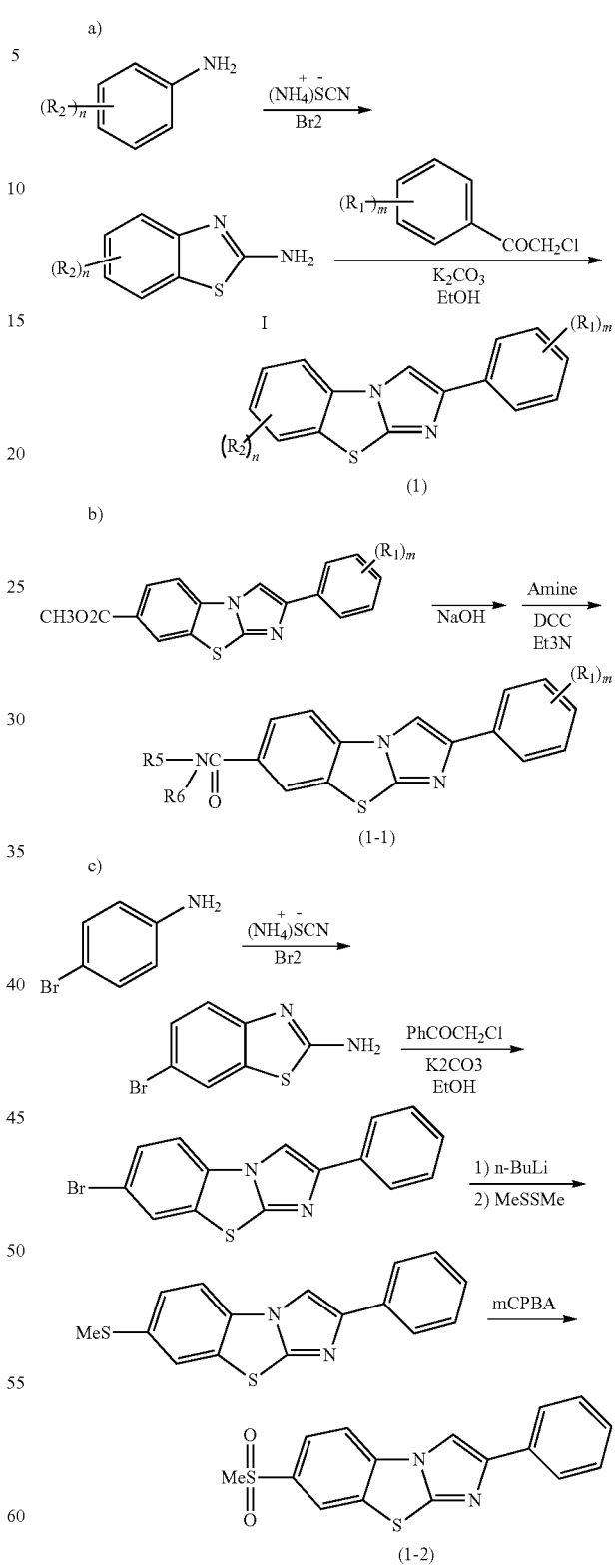

An "endoplasmic reticulum stress regulator" as used herein, refers to a substance or a composition (particularly a pharmaceutical composition) which acts to suppress or improve the accumulation of unfolded or abnormally folded protein that causes endoplasmic reticulum stress, or acts to enhance or intensify endoplasmic reticulum stress response. Consequently, the endoplasmic reticulum stress regulator of the present invention can be an agent for relieving, suppressing or improving endoplasmic reticulum stress. The endoplasmic reticulum stress regulator of the present invention can be anticipated to be used in the prevention, amelioration or treatment of neurodegenerative disease, lifestyle-related disease, cancer, autoimmune disease and the like, in which the onset of the disease is considered to be related to endoplasmic reticulum stress, by suppressing or improving endoplasmic reticulum stress.

The most desirable action for suppressing or improving endoplasmic reticulum stress, is normalizing the folding of unfolded or abnormally folded proteins. However, a similar effect can be obtained by other actions such as suppressing further folding of unfolded or abnormally folded proteins by translational repression, improving the folding efficiency of proteins by increasing or activating molecules responsible for protein folding, or promoting export of unfolded or misfolded proteins from the endoplasmic reticulum or suppressing their aggregation so as to prevent them from aggregating and possessing toxicity within the endoplasmic reticulum.

The active ingredient of endoplasmic reticulum stress regulator of the present invention desirably has a 50% inhibitory concentration ($IC_{50}$) against cell death due to endoplasmic reticulum stress under the coexistence of Tunicamycin of 20 µM or less, preferably 10 µM or less, more preferably 5 µM or less, and more preferably 1 µM or less. This value is a value measured by the method of Example 3.

The present invention also provides the use of the compound of general formula (1) for the manufacture of an endoplasmic reticulum stress regulator, compound of general formula (1) for use in a method for regulating endoplasmic reticulum stress, and a method for regulating endoplasmic reticulum stress comprising administering an effective dose of the compound of general formula (1) to a patient with a disease caused by endoplasmic reticulum stress (such as lifestyle-related disease (particularly a disease triggered by metabolic syndrome, more particularly diabetes, arteriosclerosis, hyperlipidemia and hypertension), neurodegenerative disease, cancer, and autoimmune disease) or administering it to a human with endoplasmic reticulum stress load.

An "agent for preventing, ameliorating or treating lifestyle-related disease (metabolic syndrome)" of the present invention refers to a pharmaceutical compound used for the prevention of progression and treatment of symptoms of metabolic syndrome which is caused by endoplasmic reticulum stress. Lifestyle-related disease is used as a collective term for diseases including diabetes, hyperlipidemia, hypertension, arteriosclerosis and the like, and is preferably diabetes. It is noted that as a result of diabetes, damage to pancreatic β cells becomes remarkable, and death of pancreatic β cells is eventually triggered. As a result, the secretion of insulin is reduced and interrupted, and the disease progression is accelerated. Accordingly, a means to ameliorate and treat endoplasmic reticulum stress damage to pancreatic β cells due to diabetes include accelerating the phosphorylation of eIF2α in pancreatic β cells. Therefore, the compound (1) of the present invention can have a reporter activity ($IC_{50}$) in MIN6 cell line derived from mouse pancreatic β cells of 20 µM or less, and preferably 5 µM or less.

In addition, the present invention provides use of the compound of general formula (1) for the manufacture of an agent for preventing, ameliorating or treating lifestyle-related disease (particularly diseases triggered by metabolic syndrome, more particularly diabetes, arteriosclerosis, hyperlipidemia and hypertension), as well as a compound of general formula (1) for use in a method for preventing, sty ameliorating or treating lifestyle-related disease. It also provides a method for preventing, ameliorating or treating lifestyle-related disease comprising administering to a patient with lifestyle-related disease or to a human showing signs of lifestyle-related disease an effective dose of the compound of general formula (1) for preventing, ameliorating or treating the lifestyle-related disease.

An "agent for preventing, ameliorating or treating neurodegenerative disease" of the present invention refers to a pharmaceutical compound for preventing, ameliorating or treating the symptoms of neurodegenerative diseases such as Alzheimer's disease, Parkinson's disease, polyglutamine disease, and amyotrophic lateral sclerosis (ALS).

In addition, the present invention provides use of compound of general formula (1) for the manufacture of an agent for preventing, ameliorating or treating neurodegenerative disease, as well as a compound of general formula (1) for use in a method for preventing, ameliorating or treating neurodegenerative disease. It also provides a method for preventing, ameliorating or treating neurodegenerative disease comprising administering to a patient with neurodegenerative disease or to a human showing signs of neurodegenerative disease an effective dose of the compound of general formula (1) for preventing, ameliorating or treating the neurodegenerative disease.

The present invention further provides an agent for preventing, ameliorating or treating cancer or autoimmune disease, use of compound of general formula (1) for the manufacture of an agent for preventing, ameliorating or treating cancer or autoimmune disease, as well as a compound of general formula (1) for use in a method for preventing, ameliorating or treating cancer or autoimmune disease. It also provides a method for preventing, ameliorating or treating cancer or autoimmune disease comprising administering to a patient with cancer or autoimmune disease or to a human showing signs of cancer or autoimmune disease an effective dose of the compound of general formula (1) for preventing, ameliorating or treating the cancer or autoimmune disease.

These pharmaceutical compositions can be used as oral preparations or parenteral preparations (such as injections, preparations for enteral administration via a feeding tube, suppositories, inhalants, and gargles) depending on the purpose of use. The preparations can be manufactured by formulating the above-mentioned active ingredient in the same manner as conventional pharmaceutical preparations.

Specific examples of such preparations include oral preparations such as tablets, capsules, granules, powders and syrups, injectables such as agents for intravenous injection, intramuscular injection, intradermal injection, subcutaneous injection and intrathecal injection, as well as intravenous drip infusions and the like, which are all prepared using a conventionally used pharmaceutical carrier.

Substances which are commonly used in the pharmaceutical field and which do not react with the compound of the present invention can be used as the pharmaceutical carrier. Specific examples of pharmaceutical carriers used in manufacturing tablets, capsules, granules and powders include excipients such as lactose, corn starch, sucrose, mannitol, calcium sulfate and crystalline cellulose, disintegrants such as carmellose sodium, modified starch and carmellose calcium, binders such as methylcellulose, gelatin, gum arabic, ethylcellulose, hydroxypropylcellulose and polyvinyl pyrrolidone, and lubricants such as light anhydrous silicic acid, magnesium stearate, talc and hydrogenated oils. Tablets may be coated by a known method using conventional coating agents.

Specific examples of carriers used for manufacturing syrups include sweeteners such as sucrose, glucose and fructose, suspending agents such as gum arabic, tragacanth, carmellose sodium, methylcellulose, sodium alginate, crystalline cellulose and veegum, and dispersants such as sorbitan fatty acid ester, sodium lauryl sulfate and polysorbate 80.

Injectables are usually prepared by dissolving the above-mentioned active ingredient in distilled water for injection, however, solubilizers, buffers, pH adjusters, isotonizing agents, analgesics, preservatives and the like can be added when necessary. The injectable may be in the form of a suspension injection in which the compound is suspended in distilled water for injection or vegetable oil, and when necessary, a base material, a suspending agent, a thickener and the like can be added.

The dose of the compound of the general formula (1) varies depending on the type and severity of the disease or condition, the dosage form, administration route and the like, and can be appropriately determined by those skilled in the art. For example, daily dose includes 0.00001 mg or more, 0.0001 mg or more, 0.001 mg or more, 0.01 mg or more, 0.01 mg or more, 0.1 mg or more, and 1 mg or more, and also includes 100 mg or less, 10 mg or less, 1 mg or less, 0.1 mg or less, 0.01 mg or less, 0.001 mg or less, and 0.0001 mg or less.

EXAMPLES

The present invention is explained in detail in the following examples and test examples, which however should not be construed to limit the scope of the invention.

Example 1 Establishment of Endoplasmic Reticulum Stress Reporter Cell

Figure 4:
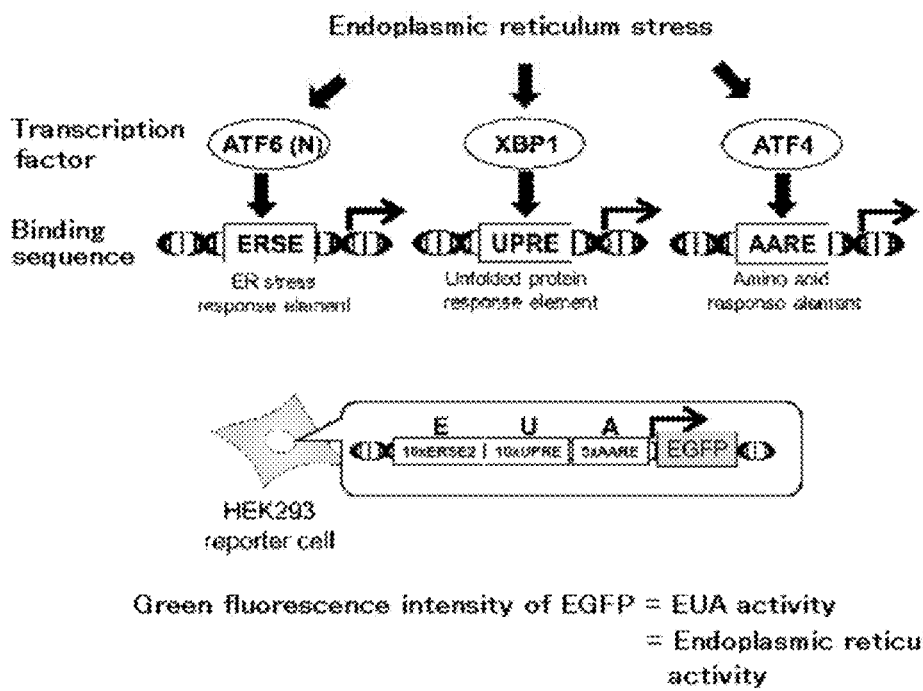
FIG. 4 depicts an overview of the cell evaluation system developed in the present invention for searching compounds having chemical chaperone activity.

As shown in FIG. 4, using a third-generation lentivirus vector, a vector comprising a sequence (10×ERSE2-10×UPRE-5×AARE-EGFP) expressing EGFP (enhanced green fluorescent protein) downstream of a tandem repeat of ER stress response element (ERSE2) targeted by ATF6, Unfolded protein response element (UPRE) targeted by XBP1 and Amino acid response element (AARE) targeted by ATF4, was generated and transduced into 293A cells.

Nucleic acid sequences encoding ERSE2, UPRE and AARE are respectively shown below.

```
ERSE2:
                              (SEQ ID NO: 1)
GGACGCCGATTGGGCCACGTTGGGAGAGTGCCT

UPRE:
                              (SEQ ID NO: 2)
CTCGAGACAGGTGCTGACGTGGCATTC

AARE:
                              (SEQ ID NO: 3)
AACATTGCATCATCCCCGC
```

Example 2 Evaluation of Chemical Chaperones for Relieving Endoplasmic Reticulum Stress Using Reporter Cells (1) Materials and Reagents Host cells: Endoplasmic reticulum stress reporter cells of Example 1 (293A transformed cells)
Tunicamycin: Wako (No. 208-08243)
Compound No. 1: Butt Park (No. 15\02-80)
Azoramide: MedChem (No. HY-18705)
Sodium 4-phenylbutyrate (4PBA): LKT Laboratories (No. P2815) Tauroursodeoxycholic Acid (TUDCA): Tokyo Kasei (No. T1567)

(2) Methods (2-1) Preparation of Reagent Solutions a) Preparation of Tunicamycin Solution 50 mg of Tunicamycin was dissolved in 25 mL, of DMSO to obtain a 2 µg/µL Tunicamycin (Tm) solution. The solution was diluted 2000-fold in DMEM solution containing 10% fetal bovine serum (FBS) to provide a 1 ng/µL Tunicamycin (Tm) solution.

b) Preparation of Compound No. 1 Solution 10 mg of Compound No. 1 was dissolved in 15 ml of DMSO to obtain a 2 mM solution.

c) Preparation of Azoramide Solution 10 mg of Azoramide was dissolved in 810 µL of DMSO to obtain a 40 mM solution.

d) Preparation of 4PBA Solution 100 mg of 4PBA was dissolved in 5.4 mL of ultrapure water to obtain a 100 mM solution.

e) Preparation of TUDCA Solution 10 mg of TUDCA was dissolved in 2 mL of ultrapure water to obtain a 100 mM solution.

2-2) Evaluation of Reporter Activity

The above compound solutions were each appropriately dissolved in DMEM solution containing 10% fetal bovine serum (FBS), and 10 µL/well were added into a 384 well assay plate. 30 µL of culture solution containing the 293A transformed cells and 10 µL of the 1 ng/µL Tm solution were then mixed together and 40 µL/well was added into the 384 well assay plate (18×10$^3$ cells/well) and incubated overnight at 37° C. Tunicamycin is a compound known to induce endoplasmic reticulum stress.

The fluorescence intensity at an excitation wavelength of 485 nm and a fluorescence wavelength of 528 nm was measured using a multiplate reader, Cytation 3 (Bio-Tek).

(2-3) Evaluation of Endoplasmic Reticulum Stress Marker Activity

ATF cell lines stably expressing EGFP (enhanced green fluorescent protein) downstream of ER stress response element (ERSE2) targeted by ATF6, Unfolded protein response element (UPRE) targeted by XBP1 and Amino acid response element (RARE) targeted by ATF4, respectively, were prepared. Compound No. 1 solutions or the like was appropriately diluted in DMEM solution containing 10% fetal bovine serum (FBS), and 10 µL/well were added into a 384 well assay plate. Further, 30 µL of culture solution containing the 293A transformed cells and 10 µL of the 1 ng/µL Tm solution were then mixed together and total 40 µL/well was added into the 384 well assay plate ($18 \times 10^3$ cells/well) and incubated overnight at 37° C. The fluorescence intensity at an excitation wavelength of 485 nm and a fluorescence wavelength of 528 nm was measured using a multiplate reader, Cytation 3 (Bio-Tek).

(3) Result

Figure 5:
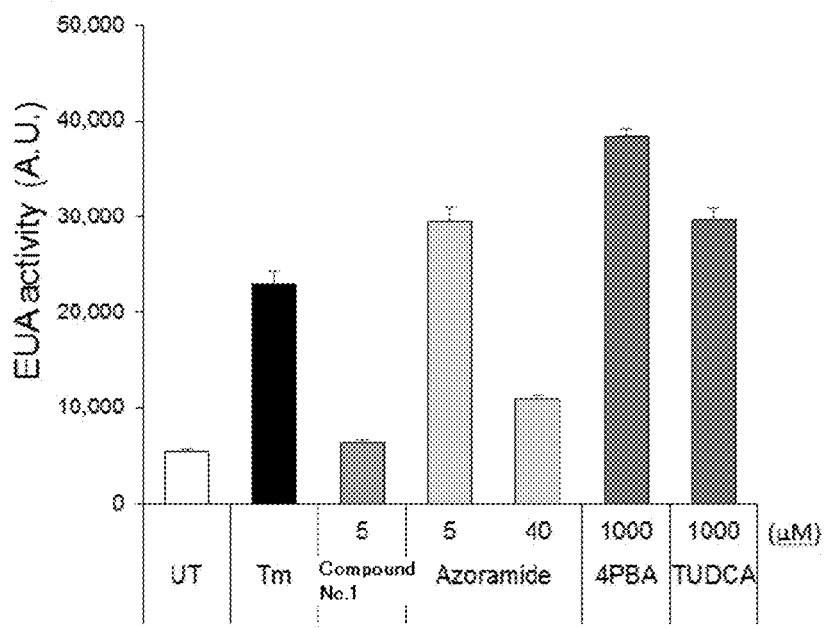
FIG. 5 depicts a comparison of Compound No. 1 with known chemical chaperone substances. Compound No. 1 was found by a screen using the cell evaluation system developed by the present inventor. 4PBA and TUDCA could not suppress EUA activity (endoplasmic reticulum stress response activation) caused by Tunicamycin (Tm), which is an endoplasmic reticulum stress inducer, whereas the modified form, Azoramide, had an inhibitory effect at 40 μM. On the other hand, Compound No. 1 had a stronger inhibitory effect at a lower concentration of 5 μM, showing that it has an unprecedented high chemical chaperone activity.

The measurement result of the fluorescence intensity is shown in FIG. 5. Each compound concentration in FIG. 5 is the final concentration. As shown in FIG. 5, Compound No. 1 almost completely inhibited the endoplasmic reticulum stress induced by Tunicamycin, and had a higher activity at a lower concentration than known chemical chaperones that relieve endoplasmic reticulum stress (Azoramide, 4PBA and TUDCA).

Figure 6:
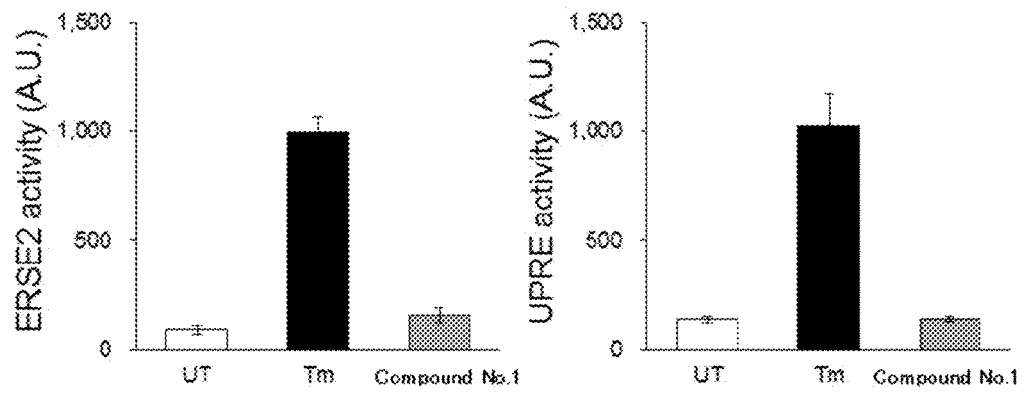
FIG. 6 shows that Compound No. 1 decreased the activity of endoplasmic reticulum stress markers (ERSE2, AARE, UPRE) that were increased by Tunicamycin, and made them recover almost completely.
Figure 6:
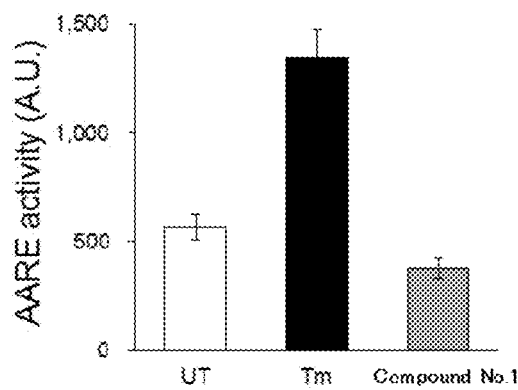

Furthermore, the measurement results of the activities of ERSE2, UPRE, and AARE are shown in FIG. 6. Compound No. 1 almost completely inhibited the activity of the target molecules of Tunicamycin-induced endoplasmic reticulum stress response, as shown in FIG. 6.

In FIG. 5 and FIG. 6, UT (Untreated), indicates that none of Tm, which is an endoplasmic reticulum stress-inducing agent, Compound No. 1, Azoramide, 4PBA, or TUDCA was added. In addition, Tm indicates that Tm (Tunicamycin solution was added as described above, however, 10 µL of Compound No. 1, Azoramide, 4PBA, or TUDCA was not added.

Example 3 Confirmation of Endoplasmic Reticulum Stress Marker Expression by Western Blotting and Measurement of Endoplasmic Reticulum Stress Inhibition Rate (1) Method Procedures according to the method for evaluating endoplasmic reticulum stress of Example 2 were carried out, and measurement of reporter fluorescence intensity as well as Western blot measurement of expression levels of endoplasmic reticulum stress markers were made to confirm the inhibition rate (chemical chaperone activity) of the compounds evaluated against endoplasmic reticulum stress induced by Tm.

Namely, a solution of Compound No. 1 listed in the list of compounds, and 4PBA, Azoramide and TUDCA solutions were respectively prepared according to item "(2-1) Preparation of reagent solutions" of Example 2.

The 293A transformed cells, were seeded into a 6 well plate at $5 \times 10^5$ cells/well, incubated overnight in a DMEM solution containing 10% fetal bovine serum (FBS).

The next day, the culture medium was changed to DMEM solution containing 10% fetal bovine serum (FBS) and 0.2 µg/ml Tm, as well as 1, 2, or 4 µM of Compound No. 1 or 10, 20, or 40 µM of AzoraMide, and incubated at 37° C. for 16 hours. After the cells were washed with PBS buffer, the cells were lysed with RIPA buffer and protein was extracted. The protein was separated according to size by SDS-PAGE electrophoresis, and endoplasmic reticulum stress marker protein was detected by Western blotting.

(2) Result a) Evaluation of Reporter Activity

EGFP fluorescence intensity was measured using multiplate reader Cytation3, for cases in which the compounds of the list of compounds were added (unit A.U.). Endoplasmic reticulum stress inhibition rates obtained from the fluorescence intensity measurements are shown in Table 2. Thus, it has become clear that the compounds have strong activity at low concentrations in which 4PBA, Azoramide and TUDCA do not show chemical chaperone activity.

TABLE 2

| Compound No. | Endoplasmic reticulum stress inhibition rate (Z)% |
|---|---|
| 1 | 100 |
| 2 | 100 |
| 3 | 101 |
| 4 | 99 |
| 5 | 79 |
| 6 | 93 |
| 7 | 95 |
| 8 | 98 |
| 9 | 61 |
| 10 | 41 |
| 11 | 66 |
| 12 | 54 |
| 13 | 60 |
| 4PBA | 0 |
| Azoramide | 0 |
| TUDCA | 0 |

[Note]
Compound concentration: 5 µM

Endoplasmic reticulum stress inhibition rate was calculated by the following equation using the fluorescence intensity measured respectively for the control solution, background evaluation solution and compound evaluation solution.

Inhibition rate (Z)=100×[1−[(Compound evaluation solution−Background evaluation solution)/(Control solution−Background evaluation solution)]]

The control solution is a solution in which Tm solution was added as mentioned above, but no compound solution of the list of compounds was added. The background evaluation solution is a solution in which neither Tm solution or compound solution of the list of compounds was added. The compound evaluation solution is solution in which Tm solution and compound solution of the list of compounds was added.

Compounds No. 2 to No. 8 of the list of compounds were exemplified as compounds having endoplasmic reticulum stress inhibition rates that were similar to the inhibition rate (chemical chaperone activity) of Compound. No. 1 shown in FIGS. 5 and 6. Some of these compounds showed higher activity at lower concentrations than known chemical chaperones that relieve endoplasmic reticulum stress (Azoramide, 4PBA and TUDCA).

b) Evaluation by Western Blotting

Figure 7:
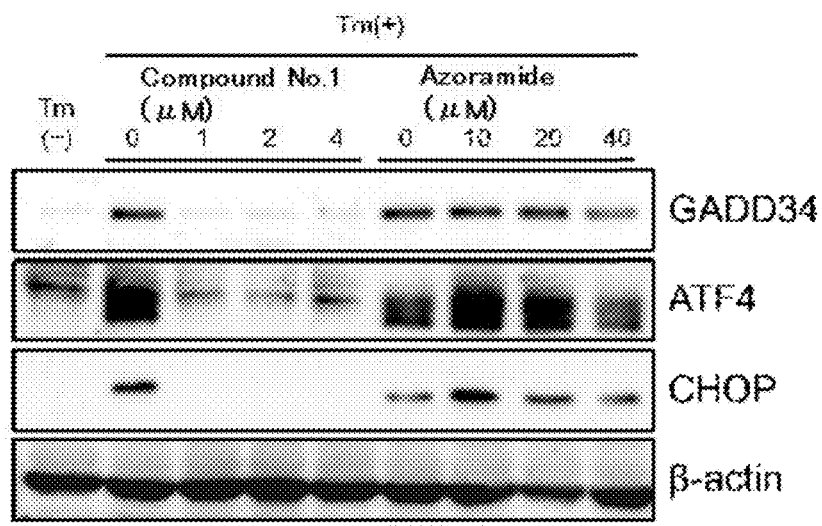
FIG. 7 depicts the result of Western blotting indicating that Compound No. 1 has a higher chemical chaperone activity than Azoramide. Compound No. 1 more strongly suppressed the induction of endoplasmic reticulum stress marker proteins GADD34 and ATF4, as well as the proapoptotic transcription factor CHOP, which are induced by the endoplasmic reticulum stress inducer Tunicamycin (Tm), at a lower concentration as compared with Azoramide.

As shown in FIG. 7, endoplasmic reticulum stress markers GADD34, ATF4 and CHOP increased as a result of Tm treatment, however, the endoplasmic reticulum stress markers (GADD34, ATF4 and CHOP) decreased when Compound No. 1 was added. This also shows that Compounds No. 1 to No. 8 relieve or suppress endoplasmic reticulum stress.

c) Evaluation of Cytoprotective Effect

The final concentration of each test compound in the compound evaluation solution was varied and viable cell count was measured to determine the 50% inhibitory concentration ($IC_{50}$) for suppressing cell death caused by Tunicamycin.

The results are shown in the following Table 3.

TABLE 3

| Compound No. | $IC_{50}(\mu M)$ |
|---|---|
| 1 | 0.61 |
| 2 | 0.34 |
| 3 | 0.43 |
| 4 | 0.41 |
| 5 | 3.7 |
| 6 | 6.7 |
| 8 | 1.6 |
| 9 | 7.4 |
| 10 | 9.2 |
| 13 | 5.0 |
| 14 | 0.01 |
| 15 | 0.01 |
| 16 | 1.2 |
| 17 | 0.7 |
| 18 | 2.6 |
| 19 | 8.0 |
| 20 | 7.8 |
| 23 | 12 |
| 24 | 7.5 |
| 25 | 0.08 |
| 4PBA | 5,400 |
| Azoramide | 86 |
| TUDCA | 2,100 |

Example 4 Cytoprotective Effect of Compound No. 1 Under Endoplasmic Reticulum Stress Conditions (1) Method According to the endoplasmic reticulum stress evaluation method of Example 2, cytoprotective effect of the evaluated sample (Compound No. 1) was confirmed under the presence of endoplasmic reticulum stress.

Namely, the 293A transformed cell line was used and treated with 0.2 μg/mL of Tm (Tunicamycin), to evaluate how cell proliferation under endoplasmic reticulum stress altered depending on the presence or absence of Compound No. 1 or Azoramide (AZO) (number of tests n=3). It is noted that in addition to Tm, camptothecin (CPT) was also used as a compound to confer cytotoxicity, and this was used as a positive control for cell death. Cell proliferation rate was determined by obtaining bright field images using a high content confocal imaging system (PerkinElmer, Operetta CLS) at intervals of 4 hours after starting the experiment, and calculating cell density from the bright field image using an image analysis software Harmony (PerkinElmer).

(2) Result

Figure 8:
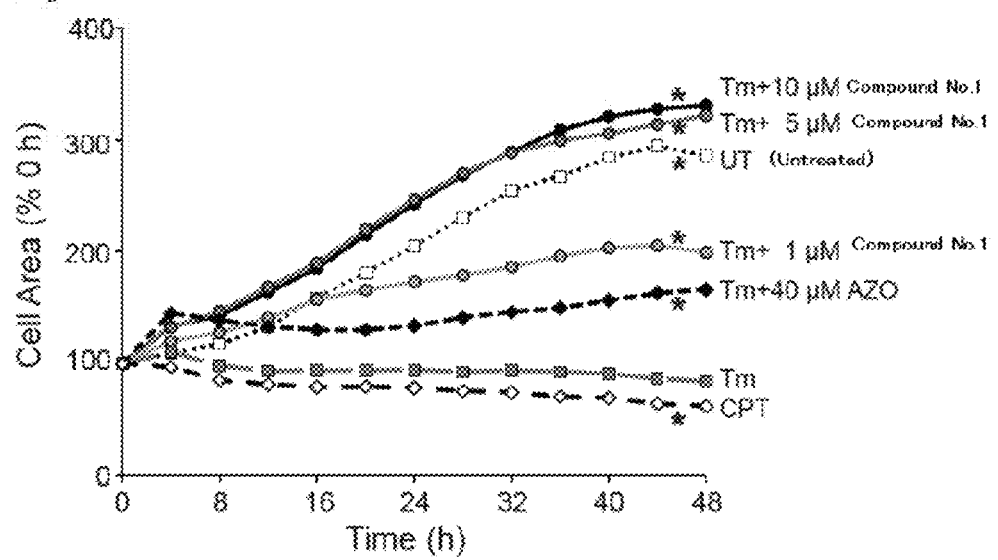
FIG. 8 depicts how cell proliferation of 293A cell line changed depending on the presence or absence of Compound No. 1, when the 293A cell line was treated with Tunicaraycin and endoplasmic reticulum stress was induced.

As shown in FIG. 8, cell proliferation was almost completely inhibited when endoplasmic reticulum stress was applied by treatment with Tm or camptothecin. However, treatment with Compound No. 1 recovered the cell proliferation dose-dependently, even when endoplasmic reticulum stress was applied by treatment with Tm. When compared with cell proliferation of Tm untreated cells (UT cells), treatment with 1 μM of Compound No. 1 solution recovered cell proliferation to approximately 70% of that of UT cells at 48 hours after treatment. When the concentration of Compound No. 1 treatment was further raised and 5 or 10 μM of the solution was added, cell proliferation recovered completely even when endoplasmic reticulum stress was applied by Tm treatment, to the same extent as that of the UT cells that were not treated with Tm.

However, cell proliferation only recovered to approximately 58% of that of UT cells, when 40 μM of Azoramide (AZO) solution was used.

Thus, the strong cytoprotective effect of Compound No. 1 against endoplasmic reticulum stress was confirmed.

Example 5 Confirmation of Cytoprotective Effect of Compound No. 1

(1) Method

Intracellular ATP level or activity of lactate dehydrogenase (LDH), which is released from cells that have been damaged in the cell membrane, were measured in order to confirm the effect of Compound No. 1 against cell growth or cytotoxicity. Namely, in a similar manner as in Example 4, the 293A transformed cell line was treated with Tm as well as Compound No. 1 or AZO, and the cells and culture medium was fractionated 43 hours after the start of the experiment. Each were measured using an ATP assay kit (Promega, Celltiter-glo) and LDH activity measurement kit (Dojindo, Cytotoxicity LDH Assay Kit-WST) using a multiplate reader, Cytation 3 (Bio-Tek) according to the protocols of the kits (number of tests n=4). As a control, intracellular ATP level and LDH activity were also measured with regard to 293A transformed cell line that was treated with only camptothecin (CPT), which is a compound that confers cytotoxicity.

(2) Result

Figure 9:
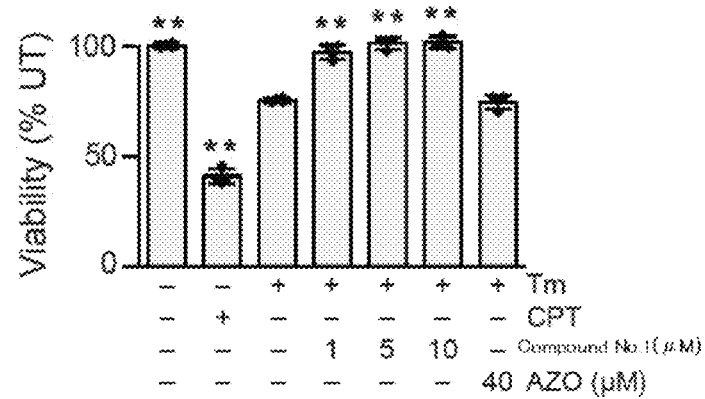
FIG. 9 depicts the evaluation of the change in intracellular ATP level, for the purpose of evaluating the endoplasmic reticulum stress suppressing effect of Compound No. 1 against cell growth or cytotoxicity that is due to the activation of endoplasmic reticulum stress response induced by Tunicaraycin treatment.

Using the level of intracellular ATP, which is the cellular energy, as an index, percentage of viable cell count of Tm untreated cells (UT cells) is shown as the viability in FIG. 9. As shown in FIG. 9, viability that decreased by Tm treatment almost completely recovered to the same extent as that of UT cells when treated with Compound No. 1. In contrast, AZO only recovered the intracellular ATP level that was decreased by Tm treatment, to approximately 75% of that of UT cells. This result is consistent with the result of the cell proliferation assay of Example 4.

Figure 10:
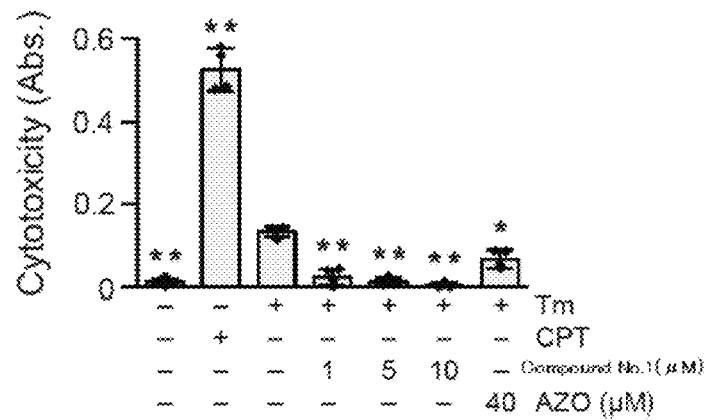
FIG. 10 depicts the evaluation of the endoplasmic reticulum stress suppressing effect of Compound No. 1 in the same manner as in FIG. 9, by measuring the activity of lactate dehydrogenase (LDH) that is released from cells that are damaged in the cell membrane. When a mutant of prion protein (PrP) overexpressed, endoplasmic reticulum stress response is activated and cell proliferation is inhibited.

Activity of lactate dehydrogenase (LDH) release from cells are shown as the cytotoxicity in FIG. 10. As shown in FIG. Compound No. 1 decreased cytotoxicity that was increased by Tm treatment, in a dose-dependent manner, and when cells were treated with 10 μM of Compound No. 1, cytotoxicity decreased completely to the same extent as that of UT cells. In contrast, AZO only decreased the LDH activity that was increased by Tm treatment, approximately 50% of that of UT cells. This result is consistent with the result of the cell proliferation assay of Example 4.

It was therefore indicated that Compound No. 1 suppressed cell growth inhibition and cell death under the presence of endoplasmic reticulum stress in a concentration-dependent manner.

Example 6 Protective Effect of Compound No 1 Against Protein Toxins

(1) Method

A prion disease model was used to evaluate the protective effect of Compound No. 1 against protein toxins in the endoplasmic reticulum. Prion disease is a neurodegenerative disease that is characterized by the accumulation of abnormally folded proteins that are different from normal prion proteins in that they are insoluble and aggregate easily, and are difficult to degrade because they are resistant to proteolytic enzymes. Prion protein (PrP protein) is produced in the endoplasmic reticulum as a secretory protein, and approximately 10% of PrP are is folded. From the findings so far, it is considered that fluctuation in endoplasmic reticulum homeostatis contribute to neurodegeneration in prion disease. Accordingly, a PrP mutant was used, in which the protein toxins in the endoplasmic reticulum induces endoplasmic reticulum stress.

In order to observe the expression level of PrP, a plasmid expressing a wild-type PrP (WT PrP) or an abnormally folded mutant PrP (mut PrP) bound to EGFP, was transfected into a 293A cell line by a conventional method using polyethylenimine (PEI). 5 µM of Compound No. 1 was also added to the culture medium of the 293A cell line expressing the abnormally folded mutant PrP (mut PrP), simultaneously with the PEI transfection. Cell proliferation rate was determined by obtaining bright field images using a high content confocal imaging system (PerkinElmer, Operetta CLS) at intervals of 4 hours after starting the experiment, and calculating cell density from the bright field image using an image analysis software Harmony (PerkinElmer).

(2) Result

Figure 11:
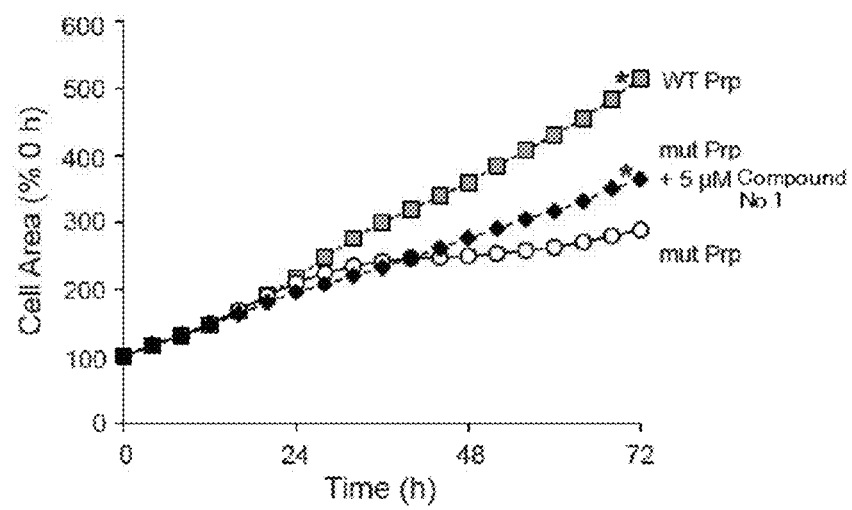
FIG. 11 depicts the evaluation of the endoplasmic reticulum stress suppressing effect of Compound No. 1 against cell proliferation inhibition caused by the overexpression of mutant PrP.

As shown in FIG. 11, cell proliferation was inhibited when mutant PrP was overexpressed. On the other hand, cell proliferation inhibition that occurred by the overexpression of mutant PrP recovered when 5 µM of Compound No. 1 solution was administered. This result is consistent with the result of the cell proliferation assay in Example 4, in which evaluation was made using a high content confocal imaging system (PerkinElmer, Operetta CLS).

Figure 12:
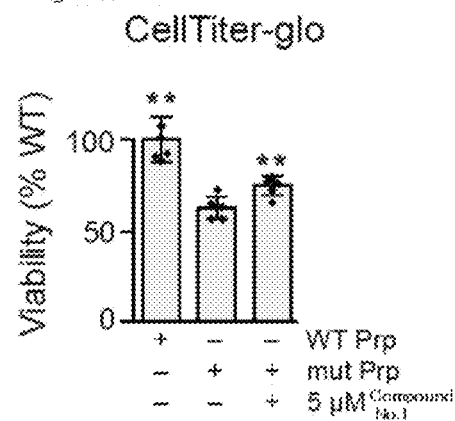
FIG. 12 depicts the evaluation of the endoplasmic reticulum stress suppressing effect of Compound No. 1, measuring the change in intracellular ATP level of cells overexpressing mutant PrP, in the same manner as in FIG. 11.

As shown in FIG. 12, it was also shown that when the cells overexpressing mutant PrP were treated with Compound No. 1, viability that decreased by the overexpression of mutant PrP was recovered, and cell growth inhibition caused by mutant PrP was improved.

Since misfolded PrP proteins cause various neurodegenerative diseases, it has been revealed that Compound No. 1 can be used as an active ingredient in agents for preventing, ameliorating or treating neurodegenerative diseases.

From the results of Examples 4 to 6, it has been revealed that Compound No. 1 protects cells under endoplasmic reticulum stress conditions.

INDUSTRIAL APPLICABILITY

The benzothiazoimidazolyl compound of general formula (1) of the present invention acts as an endoplasmic reticulum stress regulator. Consequently, the compound of the present invention can be used as an agent for preventing, ameliorating or treating various diseases that are caused by endoplasmic reticulum stress including neurodegenerative disease, lifestyle-related disease, cancer and the like. Furthermore, the compound of the present invention is an unprecedented agent for preventing, ameliorating or treating endoplasmic reticulum stress of pancreatic β cells having a novel core structure, and can be utilized as an agent for preventing, ameliorating or treating diseases including lifestyle-related disease which are caused by endoplasmic reticulum stress.

---

The invention claimed is:

1. An endoplasmic reticulum stress regulator comprising as an active ingredient a benzothiazoimidazolyl compound represented by formula (1)

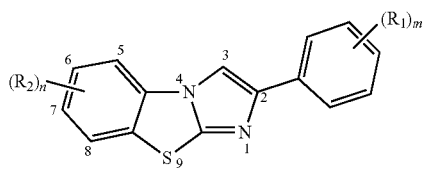

(1)

wherein:
$R_1$ represents a hydrogen atom, a halogen atom, a lower alkyl group, a lower cycloalkyl group, a lower alkanoyl group, a halogen substituted lower alkyl group, a lower alkoxy group, a halogen substituted lower alkoxy group, a cyano group, a cross-linked methylenedioxy group, an ethylenedioxy group, a propylenedioxy group, a lower alkylthio group, a lower alkylsulfonyl group, a carboxyl group, a lower alkoxycarbonyl group, an amide group, a lower alkylamide group, a lower alkylamino alkylene amide group, an amino group, an alkylamino group, a hydroxy group, a functional group represented by formula (2), or a functional group represented by formula (3)

—CONH(CH$_2$)$_p$—R$_3$ (2)

$R_3$ represents a di-lower alkylamino group, a morpholino group, a piperidino group, a 2-alkyl-piperidino group, or a 2-oxo-pyrrolidinyl group; p represents an integer from 2 to 6;

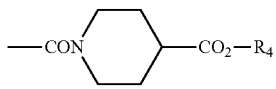

(3)

$R_4$ represents a lower alkyl group;
m represents an integer from 0 to 3;
$R_2$ represents a lower alkylsulfonyl group, a carboxyl group, a lower alkoxycarbonyl group, a functional group represented by formula (2), or a functional group represented by formula (3);
wherein the combination of the functional group represented by formula (2) and the functional group represented by formula (3) is following (A) or (B):

(A)

—CONH(CH$_2$)$_p$—R$_3$ (2)

$R_3$ represents a diethylamino group, a morpholino group, a piperidino group, a 2-methyl-piperidino group, or a 2-oxo-pyrrolidinyl group; p represents 3;

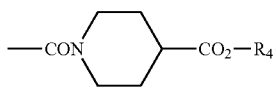

(3)

$R_4$ represents a lower alkyl group;

(B)

—CONH(CH$_2$)$_p$—R$_3$ (2)

$R_3$ represents a di-lower alkylamino group, a morpholino group, a piperidino group, a 2-alkyl-piperidino group, or a 2-oxo-pyrrolidinyl group; p represents an integer from 2 to 6;

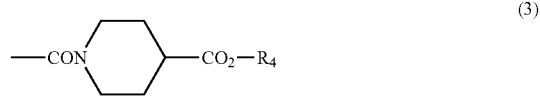

(3)

$R_4$ represents a methyl or ethyl group;
n represents an integer from 0 to 3;
the term lower represents a carbon number of 1 to 6; and
the halogen atom represents a fluorine, chlorine or bromine atom;
with the proviso that a benzothiazoimidazolyl compound represented by formula (1) wherein $R_1$ represents alkoxy group and $R_2$ represents alkylsulfonyl group is excluded.

2. The endoplasmic reticulum stress regulator according to claim 1, wherein $R_1$ is a hydrogen atom, a halogen atom, a lower alkyl group, a lower alkoxy group, a halogen substituted lower alkoxy group, a hydroxy group, or an amide group, and m is either 1 or 2.

3. The endoplasmic reticulum stress regulator according to claim 1, wherein m is 1 and $R_1$ is substituted at para-position, or m is 2 and $R_1$ is substituted at para- and meta-positions.

4. The endoplasmic reticulum stress regulator according to claim 1, wherein the halogen atom of $R_1$ is a fluorine or chlorine atom, the lower alkyl group of $R_1$ is a methyl or ethyl, and the lower alkoxy group of $R_1$ is a methoxy or ethoxy.

5. The endoplasmic reticulum stress regulator according to claim 1, wherein the lower alkylsulfonyl group of $R_2$ is a methylsulfonyl, and the lower alkoxycarbonyl group of $R_2$ is a methoxycarbonyl or ethoxycarbonyl.

6. The endoplasmic reticulum stress regulator according to claim 1, wherein n is 1, and $R_2$ is a 7-position substituent.

7. The endoplasmic reticulum stress regulator according to claim 1, wherein:
n and m are 1, and $R_1$ is a hydrogen atom, chlorine atom, fluorine atom, methyl, ethyl, difluoromethoxy, or trifluoromethoxy substituted at para-position, a fluorine atom substituted at ortho-position, or a methoxy or ethoxy substituted at meta-position, and $R_2$ is a methoxycarbonyl, ethoxycarbonyl, methyl sulfonyl, carboxyl, 3-(diethylamino)-propylamide, 3-piperidino-propylamide, 3-(2-methyl-piperidino)-propylamide, 3-morpholino-propylamide or 4-ethoxycarbonylpiperidinocarbonyl substituted at 7-position.

8. The endoplasmic reticulum stress regulator according to claim 1, wherein the 50% inhibitory concentration (IC$_{50}$) of the compound against cell death due to endoplasmic reticulum stress under the coexistence of Tunicamycin is 5 μM or less.

9. An agent for ameliorating or treating a disease selected from the group consisting of Alzheimer's disease, Parkinson's disease, polyglutamine disease, amyotrophic lateral sclerosis, diabetes, arteriosclerosis, and hypertension, comprising the endoplasmic reticulum stress regulator according to claim 1.

10. The endoplasmic reticulum stress regulator according to claim 1, wherein $R_1$ represents a hydrogen atom, a halogen atom, a lower alkyl group, a halogen substituted lower alkyl group, or a lower alkoxy group;

m and n each represent 1; and the halogen atom represents a fluorine or chlorine atom.

11. The endoplasmic reticulum stress regulator according to claim 1, wherein the compound is selected from the group consisting of:

Compound No. 1

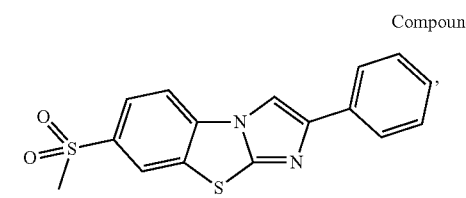

Compound No. 2

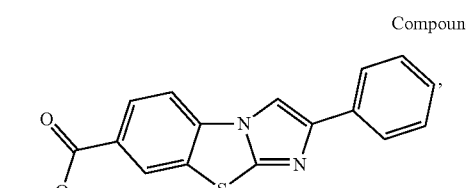

Compound No. 4

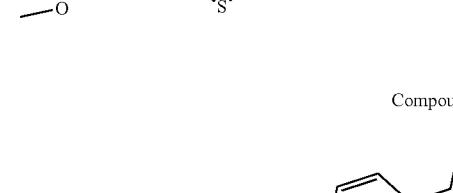

Compound No. 6

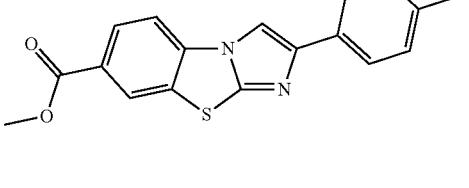

Compound No. 7

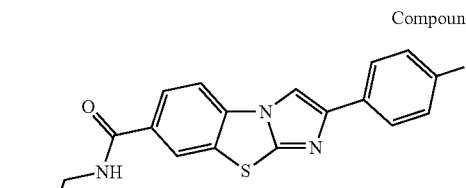

-continued

Compound No. 8

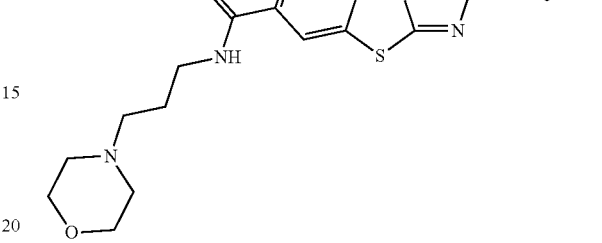

Compound No. 9

Compound No. 10

Compound No. 11

Compound No. 12

Compound No. 13

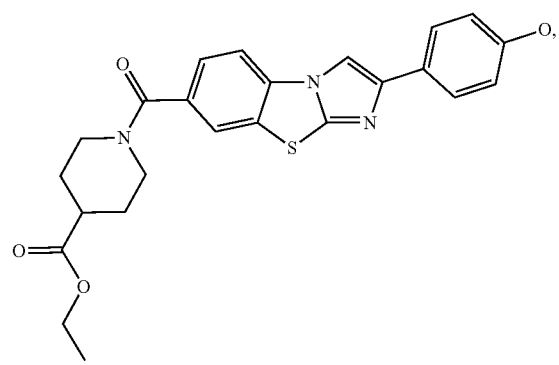

Compound No. 14

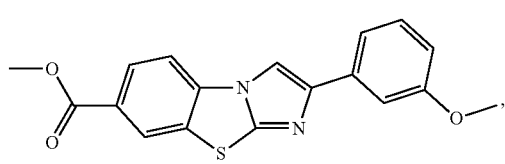

Compound No. 15

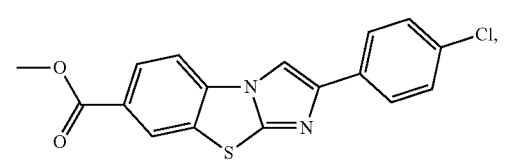

Compound No. 19

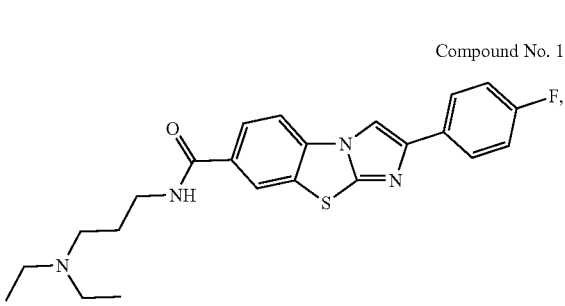

Compound No. 20

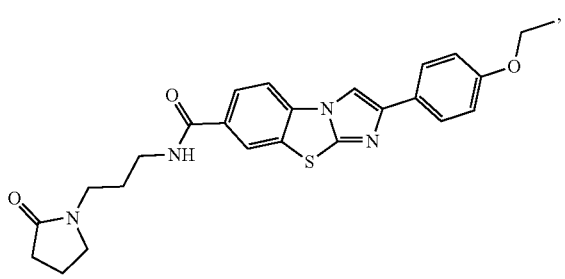

Compound No. 21

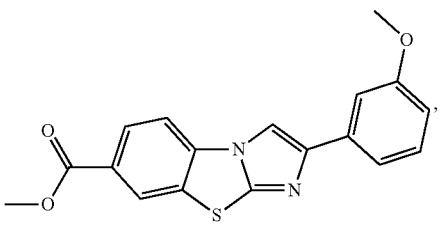

Compound No. 22

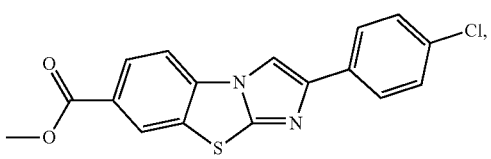

Compound No. 23

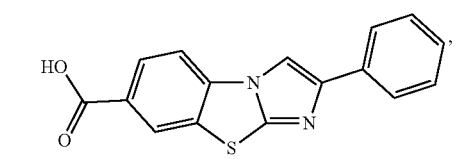

Compound No. 25

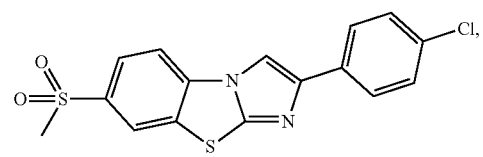

compounds of formula (4)

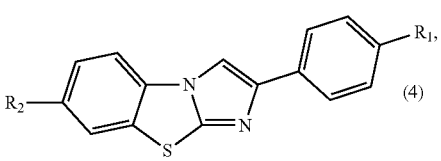

(4)

wherein $R_1$ and $R_2$ of compound No. 26 is $OCF_3$ and $SO_2CH_3$, respectively, $R_1$ and $R_2$ of compound No. 27 is chlorine atom and $SO_2C_2H_5$, respectively, $R_1$ and $R_2$ of compound No. 28 is chlorine atom and $SO_2CH(CH_3)_2$, respectively, $R_1$ and $R_2$ of compound No. 29 is chlorine atom and $CO_2H$, respectively, $R_1$ and $R_2$ of compound No. 31 is chlorine atom and $CO_2C_2H_5$, respectively, $R_1$ and $R_2$ of compound No. 32 is chlorine atom and $CO_2CH(CH_3)_2$, respectively, and $R_1$ and $R_2$ of compound No. 34 is methyl and $CO_2CH(CH_3)_2$, respectively.

* * * * *